United States Patent
Yoneta

(10) Patent No.: US 12,000,770 B2
(45) Date of Patent: Jun. 4, 2024

(54) PARTICLE SEPARATING AND MEASURING DEVICE AND PARTICLE SEPARATING AND MEASURING APPARATUS

(71) Applicant: KYOCERA Corporation, Kyoto (JP)

(72) Inventor: Masashi Yoneta, Kagoshima (JP)

(73) Assignee: KYOCERA CORPORATION, Kyoto (JP)

( * ) Notice: Subject to any disclaimer, the term of this patent is extended or adjusted under 35 U.S.C. 154(b) by 308 days.

(21) Appl. No.: 17/432,484

(22) PCT Filed: Feb. 21, 2020

(86) PCT No.: PCT/JP2020/007134
§ 371 (c)(1),
(2) Date: Aug. 19, 2021

(87) PCT Pub. No.: WO2020/175381
PCT Pub. Date: Sep. 3, 2020

(65) Prior Publication Data
US 2022/0146399 A1 May 12, 2022

(30) Foreign Application Priority Data
Feb. 27, 2019 (JP) .................................. 2019-033518

(51) Int. Cl.
*G01N 15/10* (2024.01)
*G01N 15/01* (2024.01)

(52) U.S. Cl.
CPC ... *G01N 15/1023* (2024.01); *G01N 2015/016* (2024.01); *G01N 2015/1006* (2013.01); *G01N 2015/1028* (2024.01)

(58) Field of Classification Search
CPC ......... G01N 15/1056; G01N 2015/008; G01N 2015/1006; G01N 2015/1081;
(Continued)

(56) References Cited

U.S. PATENT DOCUMENTS 8,709,825 B2 * 4/2014 Durack ................. G01N 33/48
436/63
11,421,198 B2 * 8/2022 Komori ............. B01L 3/502761
(Continued)

FOREIGN PATENT DOCUMENTS

CN 105264127 A * 1/2016 ........ B01L 3/502753
EP 3187854 A1 7/2017
(Continued)

*Primary Examiner* — Mohamed K Amara
(74) *Attorney, Agent, or Firm* — HAUPTMAN HAM, LLP

(57) ABSTRACT

A particle separating and measuring device includes a first flow path device having a post-separation flow outlet to allow discharge of a first fluid containing target particles to be separated, and a second flow path device receiving the first flow path device and having a first flow inlet to receive the first fluid. The first flow path device having a lower surface having the post-separation flow outlet is on the second flow path device having an upper surface having the first flow inlet in a first region, with the post-separation flow outlet facing and connecting to the first flow inlet. A connection flow path vertically extends from an opening of the first flow inlet to a first flow path, and narrows from the opening of the first flow inlet toward the first flow path.

8 Claims, 14 Drawing Sheets

(58) Field of Classification Search
CPC .......... G01N 15/1459; G01N 15/1484; G01N 33/491; G01N 2015/1486; G01N 2015/149; B01L 2200/027; B01L 2200/148; B01L 2200/0636; B01L 2200/0652; B01L 2300/0681; B01L 2300/0816; B01L 2300/0887; B01L 2300/168; B01L 2400/0487; B01L 3/502761

See application file for complete search history.

(56) References Cited

U.S. PATENT DOCUMENTS

| | | | |
|---|---|---|---|
| 11,446,665 B2* | 9/2022 | Koksal | ................ F17D 5/00 |
| 2003/0137666 A1* | 7/2003 | Johnson | ............ G01N 15/1459 |
| | | | 356/417 |
| 2003/0178310 A1* | 9/2003 | Gawad | ............ B01L 3/502761 |
| | | | 204/547 |
| 2004/0011975 A1* | 1/2004 | Nicoli | ................ G01N 15/0227 |
| | | | 250/574 |
| 2005/0121604 A1* | 6/2005 | Mueth | ................ A61M 1/3681 |
| | | | 250/251 |
| 2007/0242269 A1* | 10/2007 | Trainer | ............. G01N 15/0205 |
| | | | 356/336 |
| 2008/0003142 A1* | 1/2008 | Link | .................. C12N 15/1086 |
| | | | 264/219 |
| 2008/0095705 A1 | 4/2008 | Virtanen et al. | |
| 2009/0201504 A1 | 8/2009 | Ho et al. | |
| 2010/0020321 A1* | 1/2010 | Furuki | ............... G01N 15/1429 |
| | | | 356/337 |
| 2012/0225475 A1* | 9/2012 | Wagner | ................. G01N 33/487 |
| | | | 435/288.7 |
| 2013/0086980 A1 | 4/2013 | Gadini et al. | |
| 2014/0008307 A1* | 1/2014 | Guldiken | .......... B01L 3/502761 |
| | | | 422/502 |
| 2014/0261757 A1* | 9/2014 | Katsumoto | ........ G01N 15/1404 |
| | | | 137/268 |
| 2014/0273076 A1* | 9/2014 | Adams | ............... G01N 15/1434 |
| | | | 435/39 |
| 2020/0072732 A1 | 3/2020 | Hashimoto et al. | |
| 2021/0162414 A1 | 6/2021 | Liu et al. | |
| 2021/0322985 A1* | 10/2021 | Yoneta | ............. B01L 3/502761 |
| 2022/0146400 A1* | 5/2022 | Yoneta | ............. G01N 15/1056 |
| 2022/0155208 A1* | 5/2022 | Yoneta | ............. G01N 15/1484 |

FOREIGN PATENT DOCUMENTS

| | | |
|---|---|---|
| EP | 3748332 A1 | 12/2020 |
| EP | 3845309 A1 | 7/2021 |
| EP | 3859305 A1 | 8/2021 |
| EP | 3943913 A1 | 1/2022 |
| JP | 201276016 A | 4/2012 |
| WO | 2007011622 A2 | 1/2007 |
| WO | 2009012340 A2 | 1/2009 |
| WO | 2010140706 A1 | 12/2010 |
| WO | 2018216269 A1 | 11/2018 |

* cited by examiner

PARTICLE SEPARATING AND MEASURING DEVICE AND PARTICLE SEPARATING AND MEASURING APPARATUS

CROSS-REFERENCE TO RELATED APPLICATION

The present application is a National Phase entry based on PCT Application No. PCT/JP2020/007134 filed on Feb. 21, 2020, entitled "PARTICLE SEPARATION AND MEASUREMENT DEVICE, AND PARTICLE SEPARATION AND MEASUREMENT APPARATUS", which claims the benefit of Japanese Patent Application No. 2019-033518, filed on Feb. 27, 2019, entitled "PARTICLE SEPARATION AND MEASUREMENT DEVICE, AND PARTICLE SEPARATION AND MEASUREMENT APPARATUS". The contents of which are incorporated by reference herein in their entirety.

FIELD

Embodiments of the present disclosure relate generally to a particle separating and measuring device and a particle separating and measuring apparatus used to separate and measure specific particles from multiple types of particles contained in a liquid.

BACKGROUND

A known particle separating device separates and extracts particles from a liquid using a microfluidic structure (micro flow paths) several to several hundred micrometers wide and having a flow inlet and multiple flow outlets (refer to, for example, Japanese Patent Application Laid-Open No. 2012-76016). Such a particle separating device receives a liquid (e.g., blood) containing, for example, multiple types of particles (e.g., erythrocytes and leukocytes) through the flow inlet, separates target particles (e.g., leukocytes) from the liquid, and individually extracts the target particles and the other particles through the multiple flow outlets.

The separated and extracted target particles are then measured for, for example, their type, number, density, or optical properties.

SUMMARY

A particle separating and measuring device, and a particle separating and measuring apparatus are disclosed. In one embodiment, a particle separating and measuring device according to an aspect of the present disclosure includes a first flow path device that is plate-like, and including a pre-separation flow inlet to receive a fluid containing target particles to be separated, a main flow path connected to the pre-separation flow inlet, a plurality of branch flow paths connected to the main flow path, and a post-separation flow outlet to discharge a first fluid containing the target particles after being separated, and a second flow path device that is plate-like, and including a first region to receive the first flow path device, a second region to measure the target particles, a first flow inlet to receive the first fluid, a second flow inlet to receive a second fluid free from the target particles, a first flow path located in the second region and connected to the first flow inlet to allow a flow of the first fluid, and a second flow path located in the second region and connected to the second flow inlet to allow a flow of the second fluid. A lower surface of the first flow path device includes the post-separation flow outlet, and an upper surface of the second flow path device includes the first flow inlet in the first region, and the post-separation flow outlet faces and connects to the first flow inlet. The second flow path device has a connection flow path vertically extending from an opening of the first flow inlet to the first flow path, and the connection flow path having an inclined inner wall narrows from the opening of the first flow inlet toward the first flow path.

In one embodiment, a particle separating and measuring apparatus according to another aspect of the present disclosure includes the particle separating and measuring device according to the above aspect, an optical sensor that emits light toward measurement portions of the first flow path and the second flow path in the particle separating and measuring device, and receives light passing through the measurement portions of the first flow path and the second flow path, and a controller that measures the target particles by comparing an intensity of the light passing through the measurement portion of the first flow path and received by the optical sensor with an intensity of the light passing through the measurement portion of the second flow path and received by the optical sensor.

DETAILED DESCRIPTION

A particle separating device for separating target particles in a liquid includes micro flow paths including a main flow path and multiple branch flow paths connected to the main flow path. The device receives a liquid specimen containing particles to be separated as well as multiple types of particles, and also receives a fluid for generating a pressing flow from the main flow path to the branch flow paths. The liquid containing the particles separated by the particle separating device then flows into a particle measuring device, where the liquid is introduced into flow paths in a measurement portion for measurement of, for example, the density of the particles. A particle separating and measuring device combines the particle separating device and the particle measuring device connected together to perform these tasks in a series of procedures.

The particle separating and measuring device may allow a liquid containing separated particles to smoothly flow from the particle separating device into the particle measuring device with reduced particle accumulation at the joint.

In the particle separating and measuring device and the particle separating and measuring apparatus according to one or more embodiments of the present disclosure, the post-separation flow outlet in the first flow path device (particle separating device) faces and connects to the first flow inlet in the second flow path device (particle measuring device). The second flow path device has a connection flow path vertically extending from the opening of the first flow inlet to the first flow path. The connection flow path narrows from the opening of the first flow inlet toward the first flow path. This structure reduces the likelihood that target particles separated by the first flow path device accumulate at the joint between the first flow path device and the second flow path device. Thus, the first fluid containing the target particles separated by the first flow path device smoothly flows into the second flow path device to allow reliable measurement.

A particle separating and measuring device and a particle separating and measuring apparatus including the particle separating and measuring device according to one or more embodiments of the present disclosure will now be described with reference to the drawings. In one or more embodiments of the present disclosure, a Cartesian coordinate system (X, Y, Z) is defined for convenience, and the positive Z-direction is upward. However, any direction may be defined as upward or downward in one or more embodiments of the present disclosure. The embodiments below are examples of the present disclosure, and the present disclosure is not limited to the embodiments.

Particle Separating and Measuring Device

Figure 1:
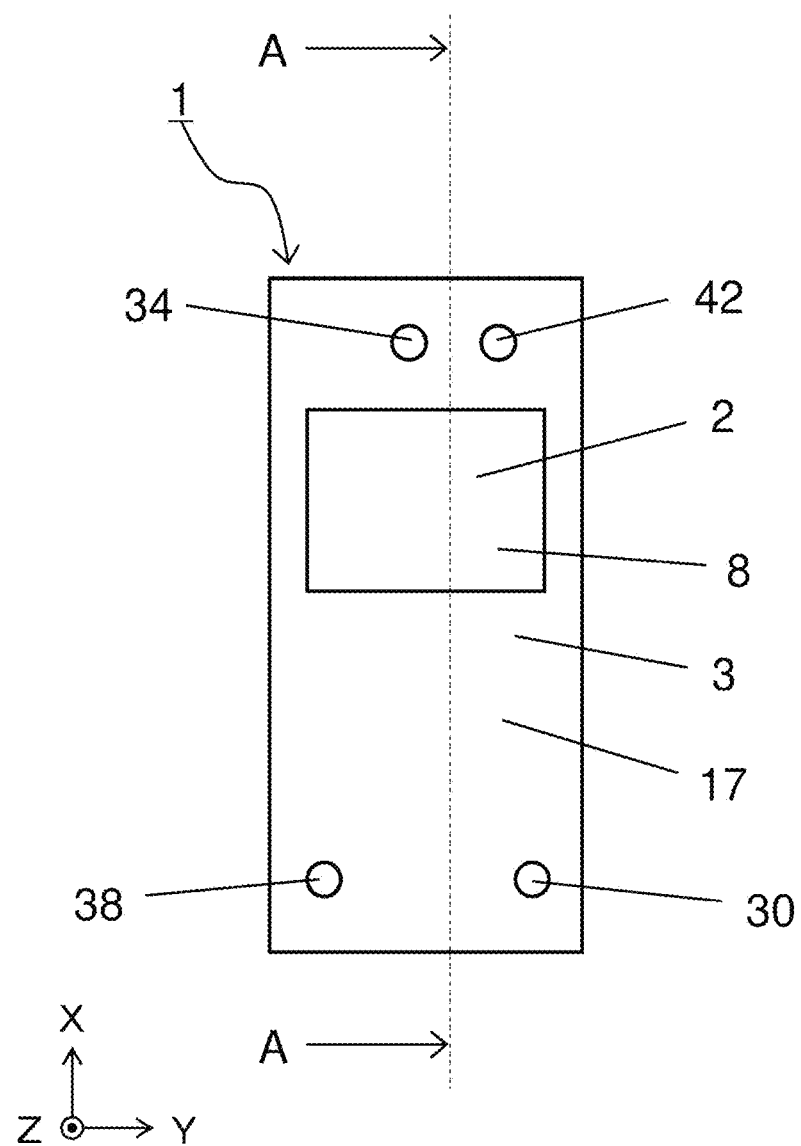
FIG. 1 illustrates a top view of an example particle separating and measuring device according to one embodiment of the present disclosure.
Figure 2:
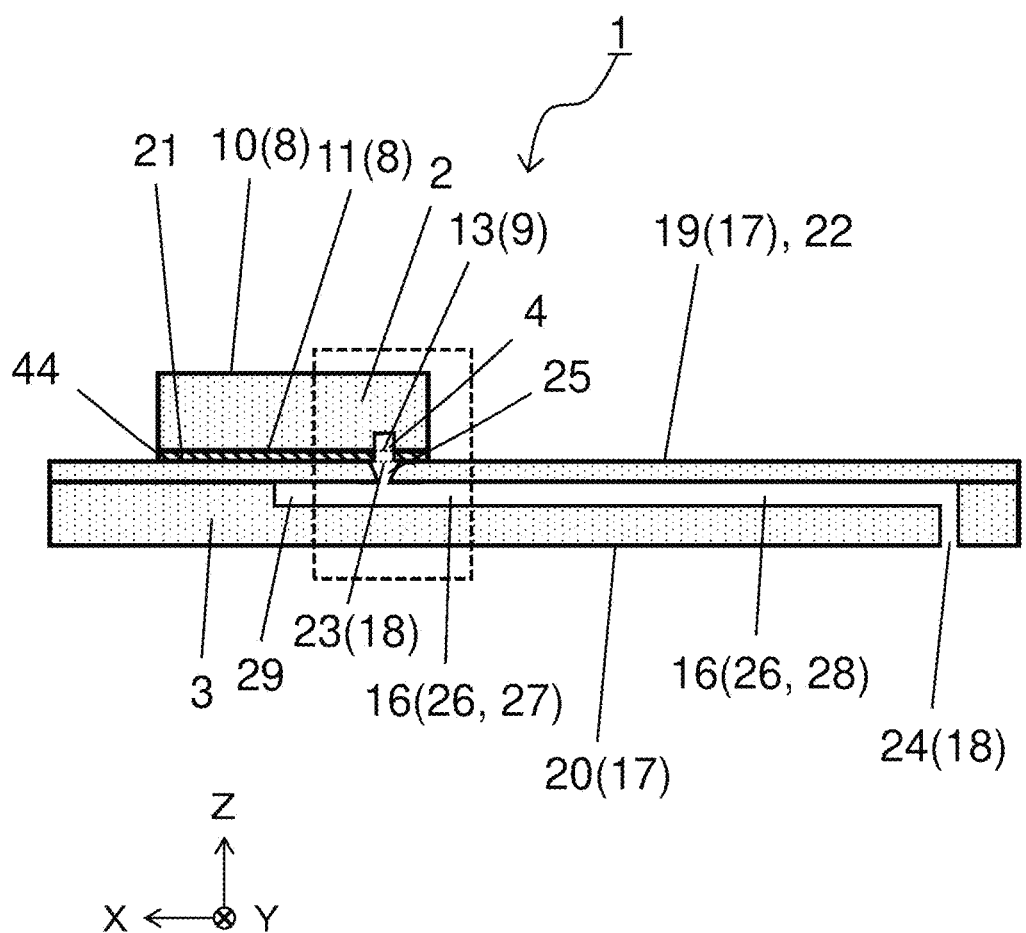
FIG. 2 illustrates a cross-sectional view of the example particle separating and measuring device according to the one embodiment of the present disclosure.

FIGS. 1 and 2 schematically show an example particle separating and measuring device according to one embodiment of the present disclosure. FIG. 1 is a top view of a particle separating and measuring device 1. FIG. 2 is a cross-sectional view of the particle separating and measuring device 1 taken along line A-A shown in FIG. 1.

In the particle separating and measuring device 1, a fluid (specimen) containing target particles to be separated flows through a first flow path device 2 as a particle separating device. The first flow path device 2 thus separates and collects the target particles. The target particles (separated particles) then flow through a second flow path device 3 as a particle measuring device connected to the first flow path device 2. The second flow path device 3 thus allows measurement of the target particles. For example, the particle separating and measuring device 1 separates and collects leukocytes as a target component from blood to allow measurement of the number of leukocytes.

Figure 3:
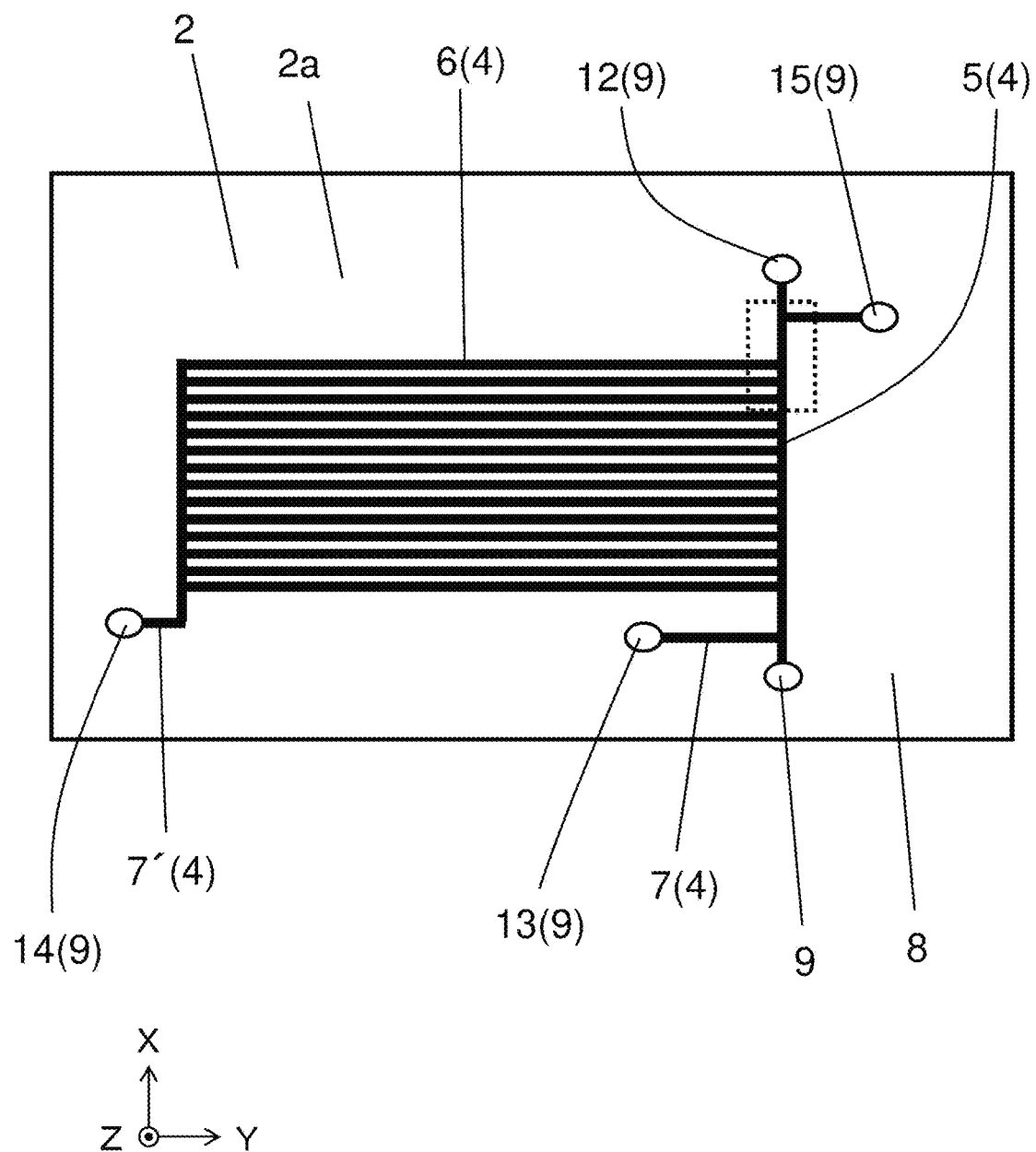
FIG. 3 illustrates a plan view of an example first flow path device in the particle separating and measuring device according to the one embodiment of the present disclosure.

FIG. 3 schematically shows the example first flow path device 2 as a particle separating device. FIG. 3 is a plan view of the first flow path device 2 in top perspective.

Particle Separating Device (First Flow Path Device)

The first flow path device 2 is a particle separating device for separating and collecting target particles from a liquid (specimen) containing multiple types of particles including the target particles to be separated. The first flow path device 2 has a pre-separation flow inlet 12 to receive a fluid containing target particles to be separated, a main flow path 5 connected to the pre-separation flow inlet 12, multiple branch flow paths 6 connected to the main flow path 5, and a post-separation flow outlet 13 to allow discharge of the first fluid containing the target particles after being separated.

The first flow path device 2 is substantially plate-like. More specifically, the first flow path device 2 includes a plate-like base 2a having a separating flow path 4 inside. The separating flow path 4 includes the straight main flow path 5 and the multiple branch flow paths 6 connected to and branching from the main flow path 5. In the first flow path device 2 according to the one embodiment of the present disclosure, a specimen (e.g., blood) flows into the main flow path 5. Then, particles (second particles, or for example, erythrocytes) different from target particles (first particles, or for example, leukocytes) flow from the main flow path 5 into the branch flow paths 6. Thus, the target particles (the first particles) in the specimen are separated. The second particles in the specimen may be separated by flowing into the branch flow paths 6.

The branch flow paths 6 branch from the main flow path 5 to receive the second particles. However, particles flowing into the branch flow paths 6 are not limited to the second particles. Particles different from the second particles (e.g., third particles) may flow into the branch flow paths 6.

Figure 4:
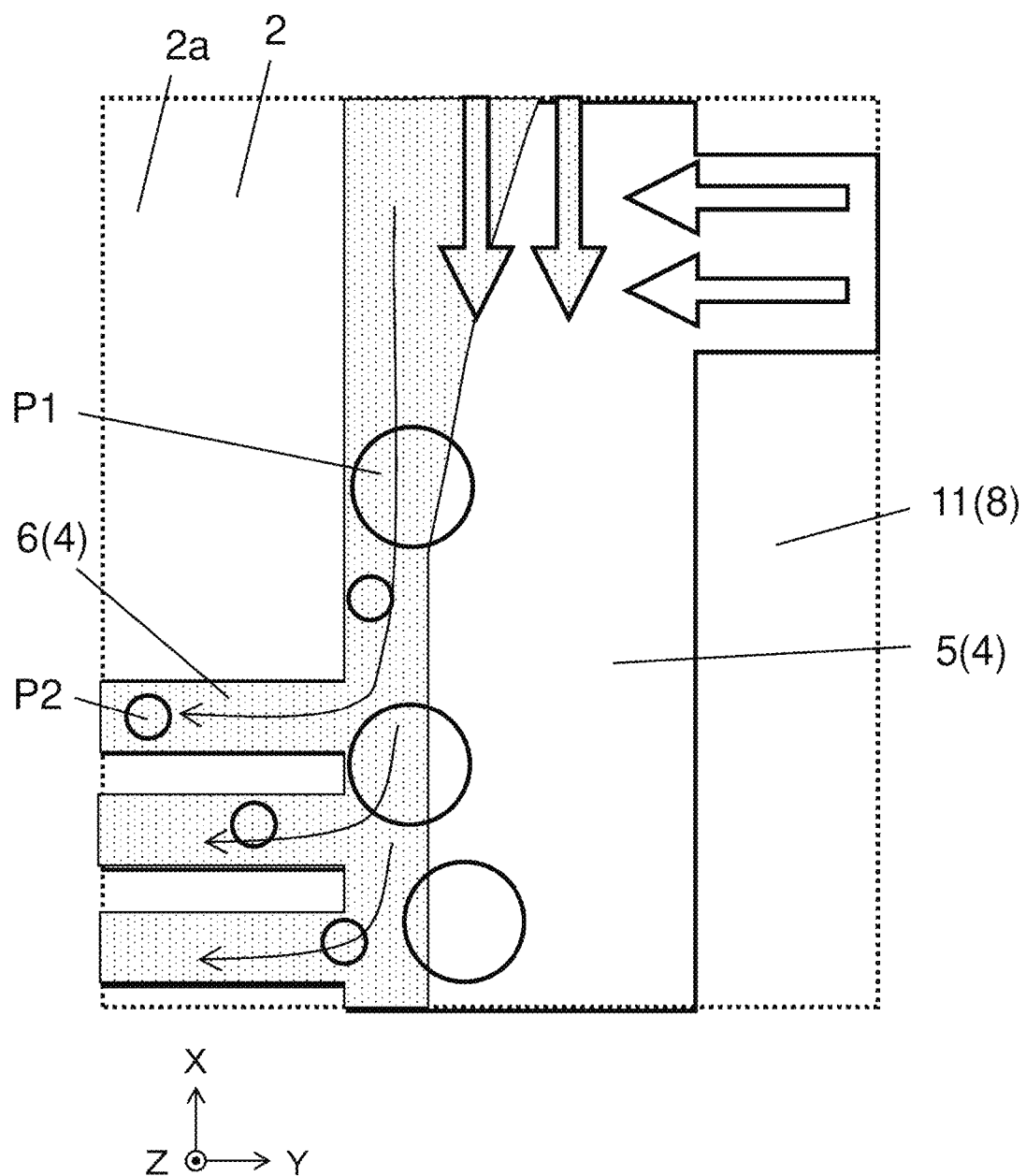
FIG. 4 illustrates a partial plan view of the example first flow path device in the particle separating and measuring device according to the one embodiment of the present disclosure.

FIG. 4 schematically shows the main flow path 5 and the branch flow paths 6 separating the first particles and the second particles. FIG. 4 is an enlarged plan view of the region enclosed by the broken line in FIG. 3. In FIG. 4, the larger circles indicate first particles P1, and the smaller circles indicate second particles P2. The hatched arrows in X-direction indicate the main flow, and the white arrows in Y-direction indicate a pressing flow (described later). The hatched region in the figure indicates a lead-in flow (described later).

The separating flow path 4 in the one embodiment of the present disclosure includes the single main flow path 5 and the multiple branch flow paths 6 orthogonal to and connected to the main flow path 5 along the main flow path 5. The first flow path device 2 generates a lead-in flow in the main flow path 5 flowing from the main flow path 5 to the branch flow paths 6 by adjusting, for example, the cross-sectional areas and the lengths of the main flow path 5 and the branch flow paths 6 and the flow velocity of the specimen. The first flow path device 2 generates a pressing flow in the separating flow path 4 for pressing the specimen through the main flow path 5 into the branch flow paths 6.

As shown in FIG. 4, the branch flow paths 6 that receive the lead-in flow each have a width smaller than the size of the first particles P1 (target particles) flowing in the specimen and larger than the size of the second particles P2 (other particles). Thus, the second particles P2 are led into the branch flow paths 6. The lead-in flow is pressed by the pressing flow and moves along the main flow path 5 adjacent to the branch flow paths 6. The lead-in flow has a width larger than the distance between the edge of the main flow path 5 and the center of gravity of the second particles P2 flowing in the specimen and smaller than the distance between the edge and the center of gravity of the first particles P1. Thus, the second particles P2 are effectively led into the branch flow paths 6. This allows the first particles P1 to be separated as target particles in the specimen and collected with the flow through the main flow path 5. This also allows the second particles P2 to be separated in the specimen and collected with the flow through the branch flow paths 6.

The first flow path device 2 according to the one embodiment of the present disclosure may be used to separate erythrocytes and leukocytes in blood as a specimen. Erythrocytes in blood have, for example, a size of 6 to 8 μm and the center of gravity 3 to 4 μm away from the edge. Leukocytes have, for example, a size of 10 to 30 μm and the center of gravity 5 to 15 μm away from the edge. In this case, the main flow path 5 may have, for example, a cross-sectional area of 300 to 1000 μm$^2$ and a length of 0.5 to 20 mm. The main flow path 5 may have, for example, a cross section having an area within the above range, a width of about 30 μm, and a height of about 20 μm. The branch flow paths 6 may each have, for example, a cross-sectional area of 100 to 500 μm$^2$ and a length of 3 to 25 mm. The branch flow paths 6 may have, for example, a cross section having an area within the above range, a width of about 15 μm, and a height of about 20 μm. The flow velocity in the separating flow path 4 may be 0.2 to 5 m/s, for example. With these dimensions, the lead-in flow may have a width of, for example, 2 to 15 μm, allowing effective separating of erythrocytes and leukocytes in blood.

The target particles may be any of various extracellular vesicles, instead of leukocytes or erythrocytes. Examples of extracellular vesicles include exosomes (30 to 200 nm), microvesicles (200 to 1000 nm), and large oncosomes (1 to 10 μm). The target particles may be inorganic matter or target fine particles in a fluid, such as a suspension containing fine powder. In either case, the separating flow path 4 may have a shape and dimensions designed as appropriate for, for example, the size of the target particles to be separated.

The first flow path device 2 has multiple first openings 9 in one or both of the upper surface and the lower surface of the base 2a. At least two of the first openings 9 are flow inlets for receiving a specimen and a fluid to flow into the main flow path 5. The flow inlets include the pre-separation flow inlet 12 and a pressing-flow inlet 15. The pre-separation flow inlet 12 receives a specimen as a fluid containing target particles (e.g., the first particles P1) to be separated, and supplies the specimen to the main flow path 5. The pressing-flow inlet 15 is orthogonally connected to a portion of the main flow path 5 upstream from and opposite to the multiple branch flow paths 6 with respect to the main flow path 5. The pressing-flow inlet 15 receives a fluid for generating a pressing flow.

The first opening 9 as the pre-separation flow inlet 12 may be circular and have a dimension of, for example, 1 to 3 mm. The flow paths in the separating flow path 4 may have the same height. The pre-separation flow inlet 12 may have a depth, for example, corresponding to the distance from the opening in the upper surface of the base 2a to the bottom surface of the main flow path 5.

The first opening 9 as the pressing-flow inlet 15 may be circular and have a dimension of, for example, 1 to 3 mm. A flow path for a pressing flow may have the same height as the other flow paths in the separating flow path 4. The pressing-flow inlet 15 may have a depth, for example, corresponding to the distance from the opening in the upper surface of the base 2a to the bottom surface of the main flow path 5.

The separating flow path 4 further includes a collection flow path 7 connected to the main flow path 5. The collection flow path 7 may be used to collect the separated first particles P1. In the separating flow path 4 in the one embodiment of the present disclosure, the first particles P1 are collected in the collection flow path 7 using a pressing flow.

The separating flow path 4 may also include a disposal flow path 7' connected to the multiple branch flow paths 6. The second particles P2 separated by the branch flow paths 6 may be collected or disposed through the disposal flow path 7'. In some embodiments, the multiple branch flow paths 6 collect the second particles P2, which are then collected in the single disposal flow path 7' connected to the branch flow paths 6. In this case, the fluid containing the first particles P1 may flow from the main flow path 5 to the collection flow path 7 and may then be disposed.

The first flow path device 2 includes the plate-like base 2a. The plate-like base 2a has the separating flow path 4 inside. The first flow path device 2 has a pair of first upper and lower surfaces 8 at the top and bottom in the thickness direction (Z-direction). The separating flow path 4 has the multiple first openings 9 in one or both of the pair of first upper and lower surfaces 8.

For convenience, one of the pair of first upper and lower surfaces 8 is referred to as a first upper surface 10 and the other as a first lower surface 11 in the one embodiment of the present disclosure. The first upper surface 10 of the pair of first upper and lower surfaces 8 is located in the positive Z-direction, and the first lower surface 11 is located in the negative Z-direction. In the one embodiment of the present disclosure, at least one of the multiple first openings 9 is located in the first lower surface 11.

The multiple first openings 9 include at least the pre-separation flow inlet 12, the post-separation flow outlet 13, and at least one disposal flow outlet 14. The pre-separation flow inlet 12 receives a specimen to flow into the main flow path 5. The post-separation flow outlet 13 discharges the first fluid containing the separated first particles P1 (target particles) for collection from the collection flow path 7. The disposal flow outlet 14 disposes, for collection, the components of the specimen excluding the first particles P1. In the one embodiment of the present disclosure, the first openings 9 include the pressing-flow inlet 15 for receiving a fluid for generating a pressing flow that presses the specimen toward the branch flow paths 6. In the one embodiment of the present disclosure, the disposal flow outlet 14 is connected to the main flow path 5 and the disposal flow path 7'. The fluid disposed through the disposal flow outlet 14 is collected through a through-hole 14' in the second flow path device 3 (described later).

The first flow path device 2 according to the one embodiment of the present disclosure is rectangular as viewed from above. The first upper and lower surfaces 8 are flat. The first flow path device 2 may not be rectangular as viewed from above. The first upper and lower surfaces 8 may not be flat. The first upper and lower surfaces 8 (the first upper surface 10 and the first lower surface 11) may have different shapes.

The first flow path device 2 is formed from, for example, polydimethylsiloxane (PDMS) or polymethyl methacrylate or acrylic resin (PMMA). The first flow path device 2 may have a thickness of, for example, 1 to 5 mm. The first flow path device 2 may be, for example, rectangular as viewed from above with short sides of 10 to 20 mm and long sides of 10 to 30 mm. The first flow path device 2 is formed by, for example, preparing two substrates, forming grooves for the separating flow path 4 on one of the substrates, and placing the other substrate to cover the grooves and bonding the substrates together to complete the base 2a having the separating flow path 4 inside.

Particle Measuring Device (Second Flow Path Device)

The second flow path device 3 is used to measure target particles separated and collected by the first flow path device 2. The second flow path device 3, together with the first flow path device 2, forms a particle separating and measuring device. The second flow path device 3 includes a first region 21 receiving the first flow path device 2, and a second region 22 defining a region to allow measurement of target particles. The second flow path device 3 also has a first flow inlet 23 to receive the first fluid, and a second flow inlet to receive a second fluid free from the target particles (described later). The second flow path device 3 also has a first flow path 16 located in the second region 22 and connected to the first flow inlet 23 to allow a flow of the first fluid, and a second flow path (described later) located in the second region 22 and connected to the second flow inlet to allow a flow of the second fluid. The second flow path device 3 is substantially plate-like.

As shown in FIG. 2, the second flow path device 3 has the first flow path 16 connected to the separating flow path 4 in the first flow path device 2. The second flow path device 3 is translucent. In the second flow path device 3, the first fluid containing target particles separated and collected by the first flow path device 2 flows through the first flow path 16, in which the target particles are measured with an optical sensor (described later). More specifically, the target particles are measured by measuring the intensity of light passing through the first fluid containing the target particles through the first flow path 16.

The second flow path device 3 includes a plate-like base having flow paths inside. The plate-like base has the first flow path 16 inside. The second flow path device 3 has a pair of second upper and lower surfaces 17 at the top and bottom in the thickness direction (Z-direction). The first flow path 16 has multiple second openings 18 in one or both of the pair of second upper and lower surfaces 17.

For convenience, one of the pair of second upper and lower surfaces 17 is referred to as a second upper surface 19 and the other as a second lower surface 20 in the one embodiment of the present disclosure. The second upper surface 19 of the pair of second upper and lower surfaces 17 is located in the positive Z-direction, and the second lower surface 20 is located in the negative Z-direction.

The second flow path device 3 according to the one embodiment of the present disclosure is rectangular as viewed from above. The second upper and lower surfaces 17 are flat. The second flow path device 3 may not be rectangular as viewed from above. The second upper and lower surfaces 17 may not be flat. The second upper and lower surfaces 17 (the second upper surface 19 and the second lower surface 20) may have different shapes.

The second flow path device 3 is formed from, for example, PMMA or cycloolefin polymer (COP). The second flow path device 3 may have a thickness of, for example, 0.5 to 5 mm. The second flow path device 3 may be, for example, rectangular as viewed from above with short sides of 20 to 40 mm and long sides of 20 to 80 mm. The second flow path device 3 is formed by, for example, preparing two substrates, forming a groove for the first flow path 16 on one of the substrates, and placing the other substrate to cover the groove and bonding the substrates together to complete the base having the first flow path 16 inside.

Figure 5:
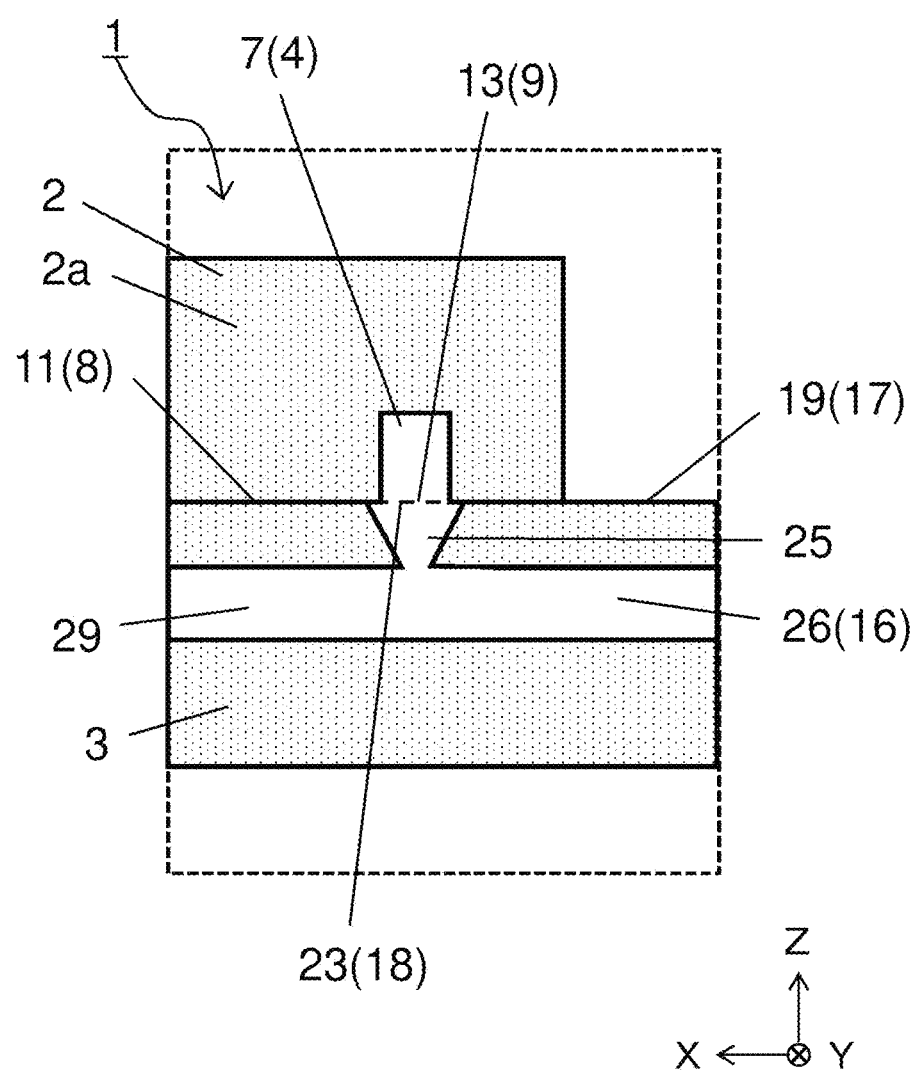
FIG. 5 illustrates a partial cross-sectional view of the example particle separating and measuring device according to the one embodiment of the present disclosure.

FIG. 5 is a partial schematic view of the example particle separating and measuring device 1 including the first flow path device 2 as a particle separating device and the second flow path device 3 as a particle measuring device. FIG. 5 is an enlarged cross-sectional view of the region enclosed by the broken line in FIG. 2.

In the second flow path device 3 according to the one embodiment of the present disclosure, at least one of the multiple second openings 18 is located in the second upper surface 19. The second upper surface 19 includes the first region 21 receiving the first flow path device 2 with the first lower surface 11 on the first region 21. One of the first openings 9 in the first lower surface 11 as the post-separation flow outlet 13 is connected to one of the second openings 18 in the second upper surface 19 as the first flow inlet 23. In the particle separating and measuring device 1 according to the one embodiment of the present disclosure, the flow path in the first flow path device 2 is directly connected to the flow path in the second flow path device 3. This allows target particles in a specimen to be separated, collected, and measured sequentially, improving processing efficiency. The particle separating and measuring device 1, in which the first flow path device 2 and second flow path device 3 are stacked in the thickness direction, is downsized.

The second flow path device 3 according to the one embodiment of the present disclosure has the second upper surface 19 including the first region 21 receiving the first flow path device 2, and the second region 22 defining the region to allow measurement of target particles. As viewed from above, the first flow path 16 in the second flow path device 3 extends over the first region 21 to the second region 22, whereas the first flow path device 2 extends in the first region 21 in the second flow path device 3 alone. The first flow path 16 is thus located in the second region 22 without overlapping the first flow path device 2. Thus, the second region 22 is used for measuring particles with the first flow path 16 used as a measurement flow path.

The particle separating and measuring device 1 may include a light reflector in the second region 22 as described later.

The first flow path device 2 and the second flow path device 3 may be formed from different materials. In the one embodiment of the present disclosure, for example, the first flow path device 2 is formed from PDMS, and the second flow path device 3 is formed from COP.

As shown in the one embodiment of the present disclosure, the first flow path device 2 is above the second flow path device 3. More specifically, the first flow path device 2 is located on the first region 21 in the second upper surface 19 of the second flow path device 3. Thus, the first fluid containing the target particles separated and collected by the first flow path device 2 efficiently flows into the second flow path device 3 using the gravity. This reduces accumulation of the first fluid containing the target particles in the flow path, for example, at a joint between the first flow path device 2 and the second flow path device 3.

The present disclosure does not exclude embodiments in which the first flow path device 2 is located on the second lower surface 20 of the second flow path device 3.

The multiple second openings 18 include the first flow inlet 23 and a first flow outlet 24. The first flow inlet 23 receives the first fluid containing the separated target particles to flow into the first flow path 16. The first flow outlet 24 discharges the first fluid from the first flow path 16 for collection. The first flow inlet 23 has an opening located in the second upper surface 19. The first flow inlet 23 faces and connects to the post-separation flow outlet 13 in the first flow path device 2. The first flow outlet 24 is located in the second lower surface 20. Thus, the first fluid smoothly enters the first flow inlet 23 from the first flow path device 2 with the gravity, facilitating collection of the first fluid at the first flow outlet 24.

Connection Structure Between First Flow Path Device and Second Flow Path Device

The first flow path device 2 is placed on the first region 21 in the second upper surface 19 of the second flow path device 3. The post-separation flow outlet 13 in the first flow path device 2 faces and connects to the first flow inlet 23 in the second flow path device 3. In the connection structure in the one embodiment of the present disclosure, as shown in FIG. 5, the second flow path device 3 has a connection flow path 25 vertically extending from the opening of the first flow inlet 23 to the first flow path 16. The connection flow path 25 narrows from the opening of the first flow inlet 23 toward the first flow path 16. The joint between the first flow path device 2 and the second flow path device 3 with this structure reduces uneven distribution of target particles in the first fluid flowing through the connection flow path 25 on the inner wall of the connection flow path 25. Thus, the first fluid flows into the first flow path 16 with reduced uneven distribution. This reduces uneven distribution of the target particles flowing from the connection flow path 25 into the first flow path 16, allowing uniform dispersion of the particles in the first flow path 16 for accurate measurement.

The post-separation flow outlet 13 may have an opening with a dimension of, for example, 0.5 to 3 mm, and more specifically, about 2 mm. The first flow inlet 23 has the opening (the entrance of the connection flow path 25) with a dimension of, for example, 0.5 to 3 mm, and more specifically, 1.5 to 2 mm. The first flow inlet 23 may have the opening larger than the opening of the post-separation flow outlet 13. The post-separation flow outlet 13 and the first flow inlet 23 may have the openings with substantially the same dimension. The openings with substantially the same dimension may include openings having dimensional differences within manufacturing tolerances. The connection flow path 25 has an opening (the exit of the connection flow path 25) with a dimension of, for example, 0.5 to 1 mm adjacent to the first flow path 16. This opening is smaller than the opening of the first flow inlet 23 (the entrance of the connection flow path 25). When the first flow inlet 23 has the opening (the entrance of the connection flow path 25) larger than the opening of the post-separation flow outlet 13, particles are less likely to accumulate at a step between the opening of the post-separation flow outlet 13 and the opening of the first flow inlet 23.

When the first flow inlet 23 has the opening (the entrance of the connection flow path 25) smaller than the opening of the post-separation flow outlet 13, particles may accumulate at a step between the opening of the post-separation flow outlet 13 and the opening of the first flow inlet 23. In this case, the connection flow path 25 allows a flow of particles to the first flow path 16 while reducing any uneven particle distribution. When the first flow inlet 23 has the opening smaller than the opening of the post-separation flow outlet 13 with a step between them, the tendency of particles to accumulate at the step depends on the characteristics of the fluid and particles or the degree of interaction between the particles and the inner walls of the flow paths. Selecting the materials or designs for the flow paths appropriately for the fluid and particles can thus reduce the susceptibility of measurement to any particle accumulation at a step to a practically negligible level, thus maintaining the effects of the one embodiment of the present disclosure.

The post-separation flow outlet 13 and the first flow inlet 23 each have a circular opening. The connection flow path 25 has a circular cross section. The cross section of the connection flow path 25 is a transverse section parallel to the XY plane. The first flow inlet 23 having the circular opening and the connection flow path 25 having a circular cross section allow the target particles contained in the first fluid to gather at and flow through the center of the connection flow path 25 without accumulating or being unevenly distributed. The connection flow path 25 may have the shape varying substantially linearly. More specifically, the connection flow path 25 may have the inner wall inclined substantially linearly. The connection flow path 25 may have a bowl shape having the inclination or diameter decreasing from the entrance (the opening of the first flow inlet 23) to the exit (the joint with the first flow path 16) at a decrease rate gradually increasing from the entrance to the exit. In this case, the connection flow path 25 has the inner wall vertically curved. Thus, the connection flow path 25 can hold the target particles contained in the first fluid before the fluid passes. This allows a stable flow of the first fluid and can easily adjust the time for supplying the first fluid to the first flow path 16, as compared with the connection flow path 25 having a linearly varying inner wall.

The opening of the post-separation flow outlet 13, the opening of the first flow inlet 23, and the cross section of the connection flow path 25 may have other shapes depending on the characteristics of the target particles and the first fluid. For example, they may be elliptic or rectangular, or specifically, square, rectangular, or rhombic. For elliptic shapes, the minor axes may align with the direction in which any other flow paths are located near the openings, and the major axes may align with the direction in which sufficient space is provided around the openings. This flow path can have less interference with other flow paths. For rhombic shapes, the first fluid can be easily controlled to have different flow velocities between the central portion and the peripheral portion. This may allow flow control at the joint.

The post-separation flow outlet 13 and the first flow inlet 23 basically concentrically face each other. However, the post-separation flow outlet 13 and the first flow inlet 23 may face each other with their centers either being misaligned within manufacturing tolerances in assembly or being out of alignment. When the post-separation flow outlet 13 has its center offset downstream along the first flow path 16 relative to the center of the first flow inlet 23, the first fluid tends to more easily flow downstream along the first flow path 16 due to, for example, the flow of the second fluid (described later).

The first flow path 16 connected to the connection flow path 25 includes a planar portion 26, which is connected to the connection flow path 25 and extends in a direction in a plane over the second region 22. The first flow path 16 connected to the connection flow path 25 reduces accumulation of the first fluid at the joint with the separating flow path 4, and also reduces the uneven distribution of the separated target particles. The first flow path 16 can hold the first fluid in the planar portion 26 for measurement of particles, thus allowing reliable measurement.

The connection flow path 25 may have a width (dimension of the exit) of, for example, 0.5 to 1 mm at the joint with the first flow path 16 as described above. The planar portion 26 may have a width of, for example, 1.5 to 6 mm. The connection flow path 25 may have a length of, for example, 0.5 to 1 mm. The planar portion 26 may have a height of, for example, 0.5 to 2 mm.

In the example shown in FIG. 2, a sheet member 44 is placed between the first flow path device 2 and the second flow path device 3. The sheet member 44 is optional and may not be included as in the example shown in FIG. 5. The first flow path device 2 and the second flow path device 3 may be directly connected to each other with a silane coupling agent applied to one or both of the first lower surface 11 of the first flow path device 2 and the second upper surface 19 of the second flow path device 3.

Figure 6:
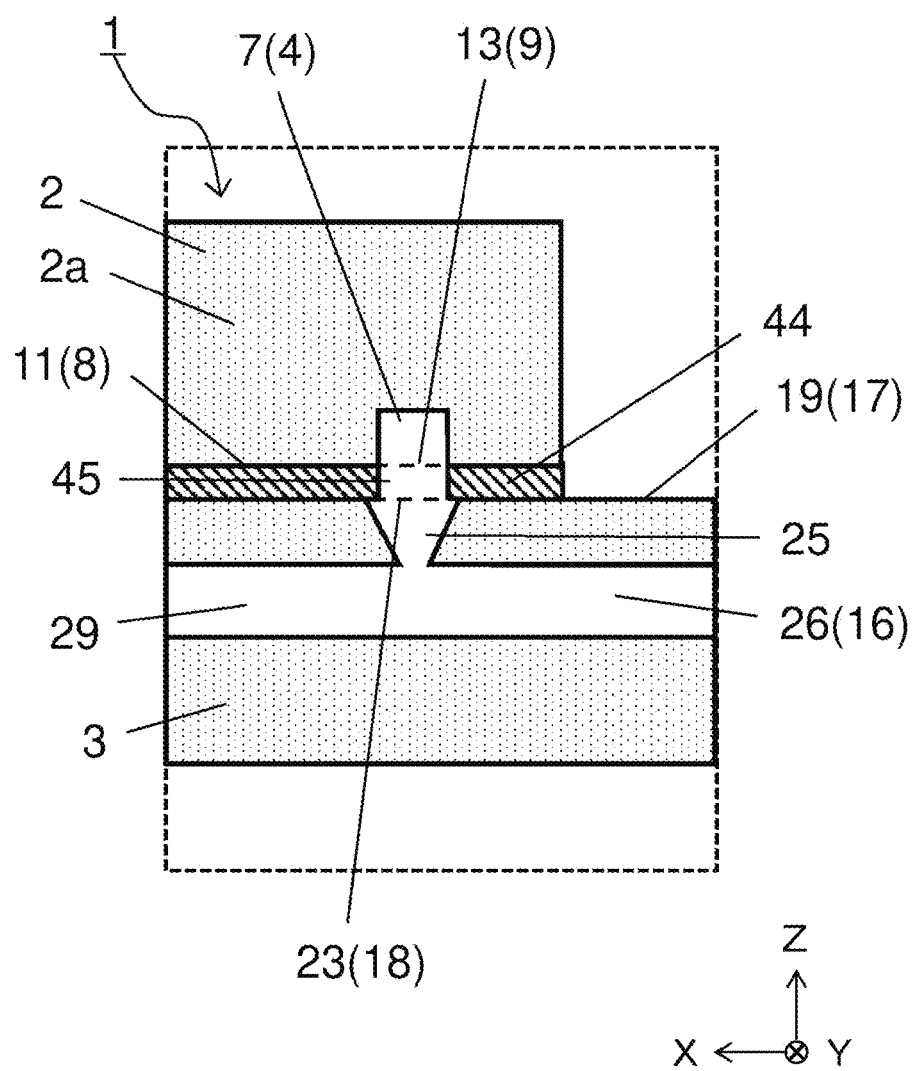
FIG. 6 illustrates a partial cross-sectional view of an example particle separating and measuring device according to the one embodiment of the present disclosure.

As in a cross-sectional view of FIG. 6 similar to FIG. 5, the sheet member 44 may be placed between the first lower surface 11 of the first flow path device 2 and the second upper surface 19 of the second flow path device 3, as in the example shown in FIG. 2. In other words, the particle separating and measuring device 1 may include the sheet member 44 between the first flow path device 2 and the second flow path device 3. More specifically, the first flow path device 2 may be placed on the second flow path device 3 with the sheet member 44 in between, and the post-separation flow outlet 13 and the first flow inlet 23 may connect to each other with a through-hole 45 in the sheet member 44. The through-hole 45 in the sheet member 44 may have an opening with substantially the same dimension as the opening of the post-separation flow outlet 13. The through-hole 45 in the sheet member 44 may have the opening smaller than the opening of the first flow inlet 23.

For the first flow path device 2 and the second flow path device 3 formed from materials that are difficult to adhere to each other, the sheet member 44 as an intermediate layer can firmly bond the devices, thus stably forming the particle separating and measuring device 1. The through-hole 45 between the post-separation flow outlet 13 and the first flow inlet 23 may have the opening with an appropriate dimension that falls between the dimensions of the openings of the post-separation flow outlet 13 and the first flow inlet 23. This effectively prevents accumulation of the first fluid and the target particles at the joint between the first flow path device 2 and the second flow path device 3.

The sheet member 44 reduces leakage of, for example, the first fluid from the bonding surfaces of the first flow path device 2 and the second flow path device 3. The sheet member 44 also serves as an intermediate layer for bonding materials that are difficult to adhere to each other. The sheet member 44 may be of a material such as silicone or PDMS. The sheet member 44 also accommodates any deformation of the first lower surface 11 and the second upper surface 19 as bonding surfaces. The sheet member 44 may have multiple through-holes as appropriate, in addition to the through-hole 45 between the post-separation flow outlet 13 and the first flow inlet 23. The multiple through-holes, including the through-hole 45, face multiple first openings 9 and second openings 18. The fluid thus flows from the first flow path device 2 through these through-holes to the second flow path device 3.

The sheet member 44 may have a thickness of, for example, about 0.5 to 3 mm. The sheet member 44 having a thickness of about 2 mm can sufficiently accommodate any deformation of the bonding surfaces, and also shorten the distance between the post-separation flow outlet 13 and the first flow inlet 23. The sheet member 44 with such a thickness can also reduce cracks or other damage when the first flow path device 2 and the second flow path device 3 are bonded together.

The sheet member 44 may have any appropriate dimensions (area) large enough for adhesion around the through-hole 45 and smaller than or equal to the dimensions of the first lower surface 11 of the first flow path device 2. The sheet member 44 may not be a single sheet, and may be a combination of multiple sheets with predetermined shapes and dimensions.

The first flow path device 2 and the second flow path device 3 according to the one embodiment of the present disclosure may be directly connected to the sheet member 44, or may be connected with an adhesive applied to the upper and lower surfaces of the sheet member 44. The adhesive may be, for example, a photo-curable resin curable with ultraviolet light or a thermoplastic resin.

Figure 7:
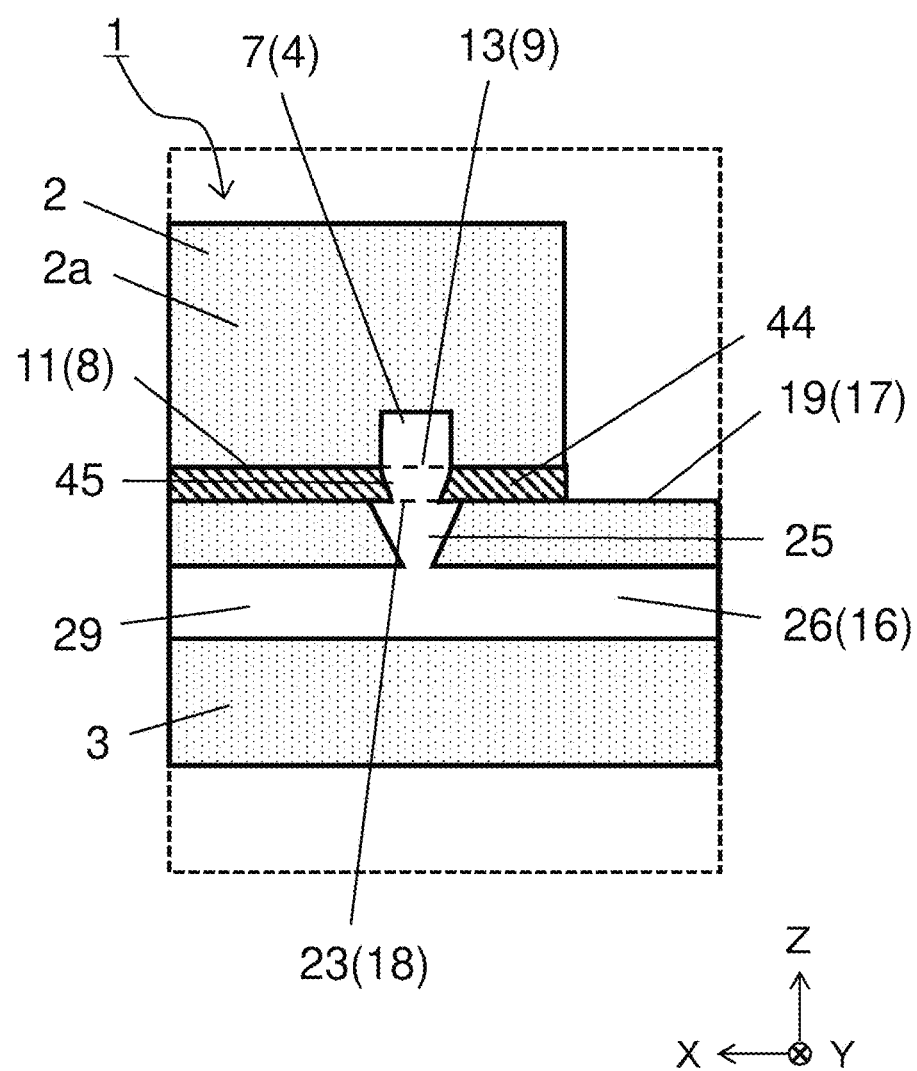
FIG. 7 illustrates a partial cross-sectional view of an example particle separating and measuring device according to the one embodiment of the present disclosure.

In the particle separating and measuring device 1 according to the one embodiment of the present disclosure, the through-hole 45 in the sheet member 44 may narrow from the post-separation flow outlet 13 toward the first flow inlet 23, as in a cross-sectional view of FIG. 7 similar to FIG. 6. In the present example, the through-hole 45 has an opening adjacent to the post-separation flow outlet 13 with substantially the same dimension as the opening of the post-separation flow outlet 13. The through-hole 45 has an opening adjacent to the first flow inlet 23 smaller than the opening of the first flow inlet 23. For example, the through-hole 45 has the opening adjacent to the post-separation flow outlet 13 with a dimension of about 2 mm, and the opening adjacent to the first flow inlet 23 with a dimension of about 1.7 mm. The structure with such dimensions effectively reduces accumulation of the first fluid at the joints between the post-separation flow outlet 13, the through-hole 45, and the first flow inlet 23 when the first fluid flows through them. In this case, the through-hole 45 may have, instead of the straight inner wall shown in FIG. 7, a curved inner wall that narrows from the post-separation flow outlet 13 toward the first flow inlet 23 in cross section.

The particle separating and measuring device 1 according to the one embodiment of the present disclosure may include, between the first flow path device 2 and the second flow path device 3, the sheet member 44 having a higher hardness than the first flow path device 2 and a lower hardness than the second flow path device 3. This allows the flow path in the softer first flow path device 2 to maintain its shape on the flat, harder base sheet member 44 between the first flow path device 2 and the sheet member 44. The sheet member 44 is tightly as well as firmly bonded to the second flow path device 3, serving as the harder base, between the second flow path device 3 and the sheet member 44. The bonding surfaces of the first flow path device 2 and the sheet member 44 may have substantially the same surface roughness. The bonding surfaces of the sheet member 44 and the second flow path device 3 may have substantially the same surface roughness. More specifically, these bonding surfaces may have an arithmetic mean roughness Ra of about 0.005 to 0.05 μm.

To evaluate the hardness of the components, International Rubber Hardness Degrees (IRHD) are typically used for rubber molded products, and Rockwell hardness for resin molded products. The hardness of the components herein can be measured with IRHD for relative evaluation. For example, the first flow path device 2 may have a hardness of at least 30 and lower than 80 under IRHD, the sheet member 44 may have a hardness of about 80 under IRHD, and the second flow path device 3 may have a hardness of higher than 80 under IRHD. For example, the first flow path device 2 may be formed from PDMS, the sheet member 44 from silicone, and the second flow path device 3 from COP or PMMA to achieve a combination of the above hardness. More specifically, PDMS is about 30 under IRHD, silicone is about 80 under IRHD, and COP exceeds 80 under IRHD (about 50 in Rockwell hardness). These materials may be used to achieve a combination of the above hardness.

The hardness can be measured by pressing an unsharp indenter into an object to be measured with a predetermined force, and measuring and quantifying its deformation. For durometer hardness, the force for pressing the indenter is applied with a spring. For IRHD, the force for pressing the indenter is applied with, for example, a weight for applying a constant load. Durometer hardness, which can be measured with a simpler instrument, is more common and may be used in the one embodiment.

Figure 8:
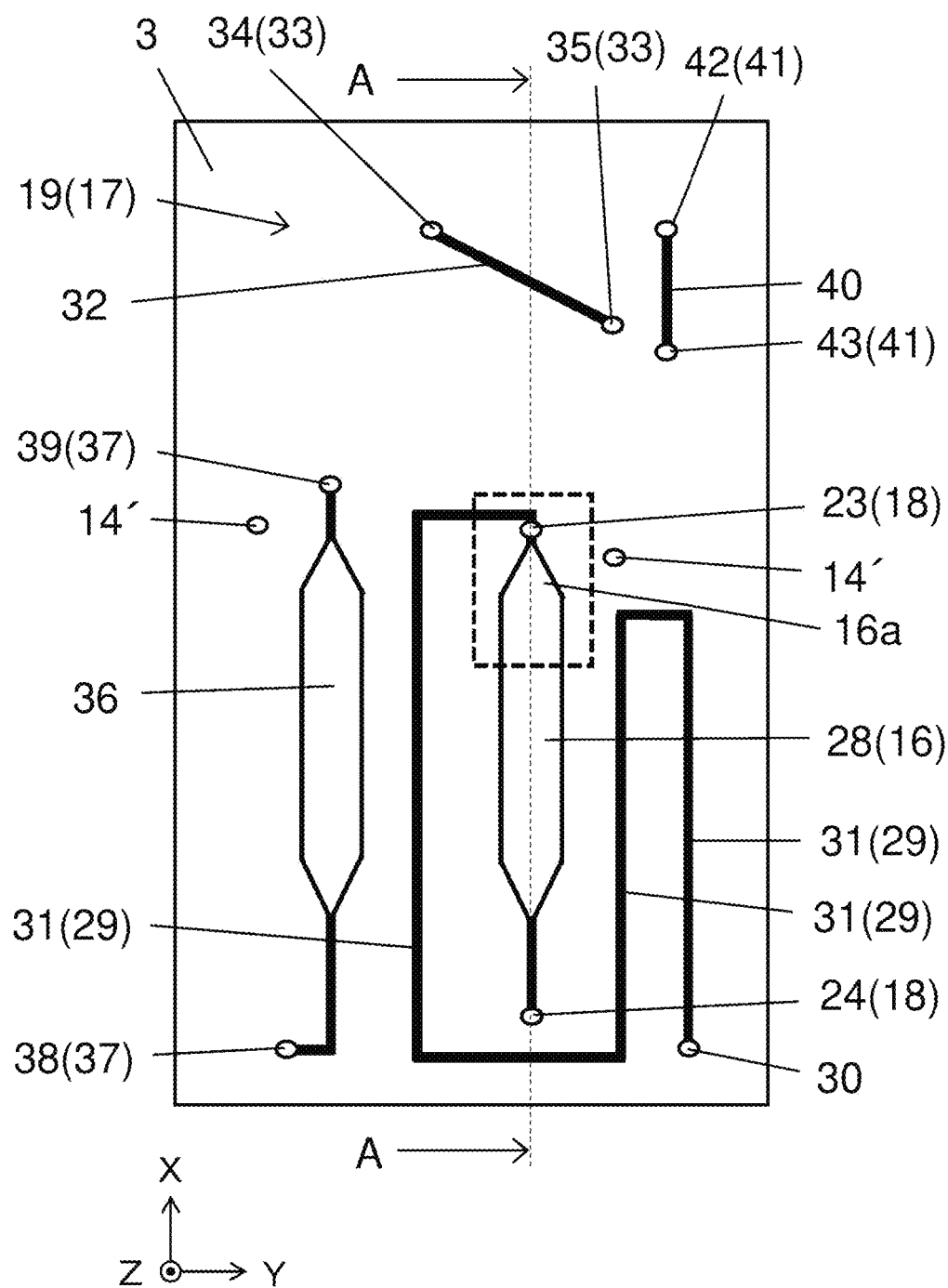
FIG. 8 illustrates a plan view of an example second flow path device in the particle separating and measuring device according to the one embodiment of the present disclosure.
Figure 9:
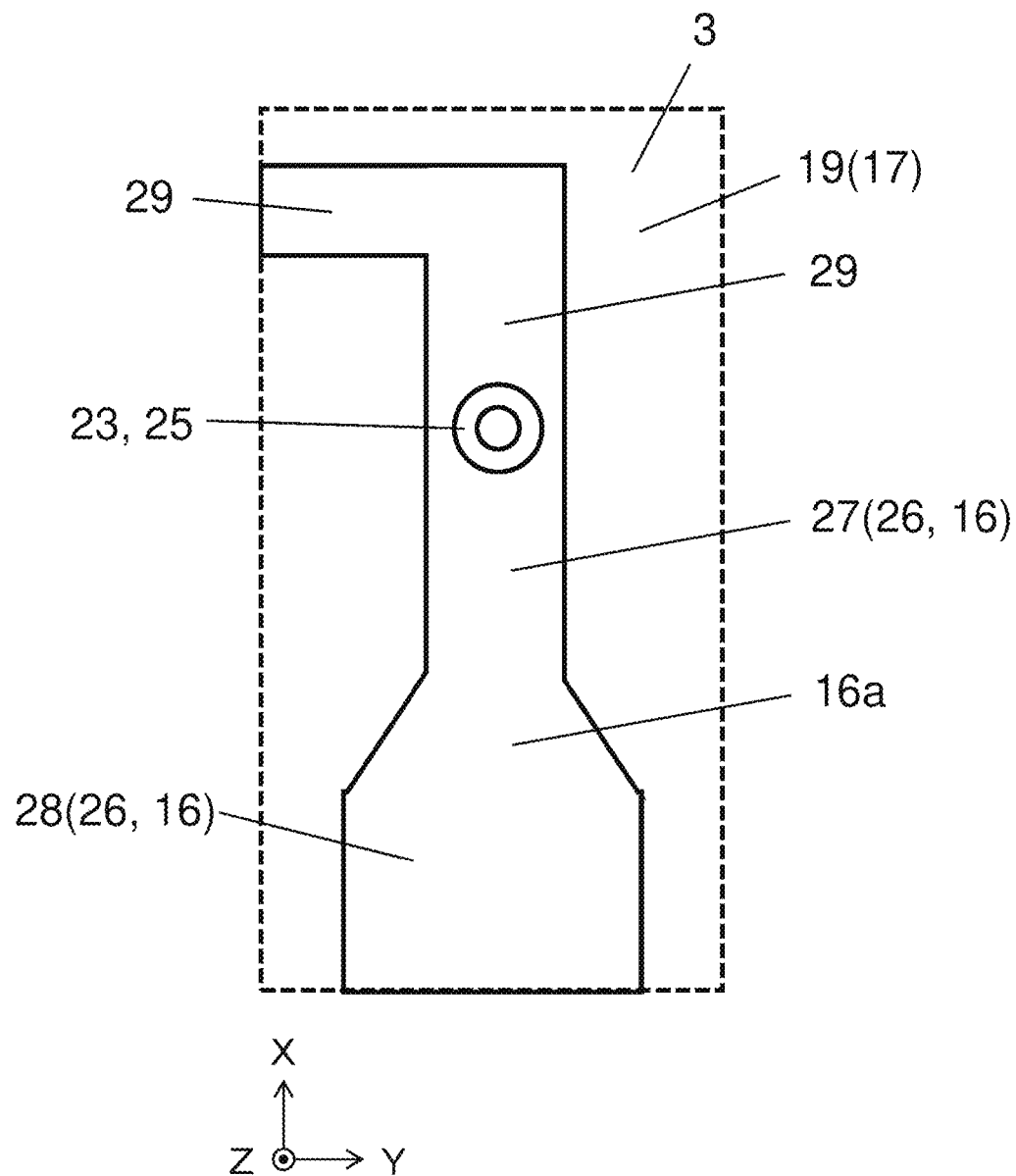
FIG. 9 illustrates a partial plan view of the example second flow path device in the particle separating and measuring device according to the one embodiment of the present disclosure.

FIGS. 8 and 9 schematically show the example second flow path device 3 included in the particle separating and measuring device 1. FIG. 8 is a plan view of the second flow path device 3 in top perspective. FIG. 9 is an enlarged plan view of the region enclosed by the broken line in FIG. 8. Line A-A in FIG. 8 is at the same position as line A-A in FIG. 1.

The planar portion 26 in the first flow path 16 may have a greater width than the connection flow path 25 at least at the joint with the connection flow path 25. This structure reduces accumulation of the first fluid at the joint between the planar portion 26 and the connection flow path 25.

The planar portion 26 may include a first planar portion 27 connected to the connection flow path 25, and a second planar portion 28 connected to the first planar portion 27 and having a greater width than the first planar portion 27. The first planar portion 27 and the second planar portion 28 may be connected to each other with a width-increasing portion 16a in between. The width-increasing portion 16a has a flow path width increasing downstream along the flow of the first fluid from the joint between the connection flow path 25 and the first flow path 16. More specifically, the second flow path device 3 may include the width-increasing portion 16a between the first flow inlet 23 and the second planar portion 28 located in the second region 22 and used as the measurement portion in the first flow path 16. The width-increasing portion 16a has a flow path width increasing downstream along the flow of the first fluid. The width-increasing portion 16a causes a flow of the first fluid to spread in the width direction to disperse the target particles contained in the first fluid. This structure reduces unevenness of the target particles for measurement. This facilitates, in the second planar portion 28, diffusion of particles (e.g., the first particles P1) separated and collected by the first flow path device 2.

The first planar portion 27 may have a width of, for example, 0.5 to 3 mm. The second planar portion 28 may have a width of, for example, 1 to 5 mm. The second planar portion 28 may have a width of, for example, 2 to 10 times the width of the first planar portion 27. In the one embodiment of the present disclosure, the width-increasing portion 16a has a width gradually increases at the joint between the first planar portion 27 and the second planar portion 28. In other words, the width-increasing portion 16a is flared in the width direction. The flared portion widens toward the end at 20 to 40° on each side of the centerline across the width of the planar portion 26 (the first planar portion 27 and the second planar portion 28). The flared portion may have a length of about 3 to 5 mm.

The width-increasing portion 16a may widen in a curved or stepwise manner, rather than widening gradually in a straight manner. The width-increasing portion 16a connecting the first planar portion 27 to the second planar portion 28 may have a flow path width increasing stepwise, for example, from 1 mm to 2.5 mm, and from 2.5 mm to 5 mm. The width-increasing portion 16a having such a sharply increasing flow path width allows the second planar portion 28 to have a flow path width twice or more that of the first planar portion 27. This allows a vortex to occur in the first fluid flowing through these portions, facilitating agitation and mixing of the target particles contained in the first fluid.

Figure 10:
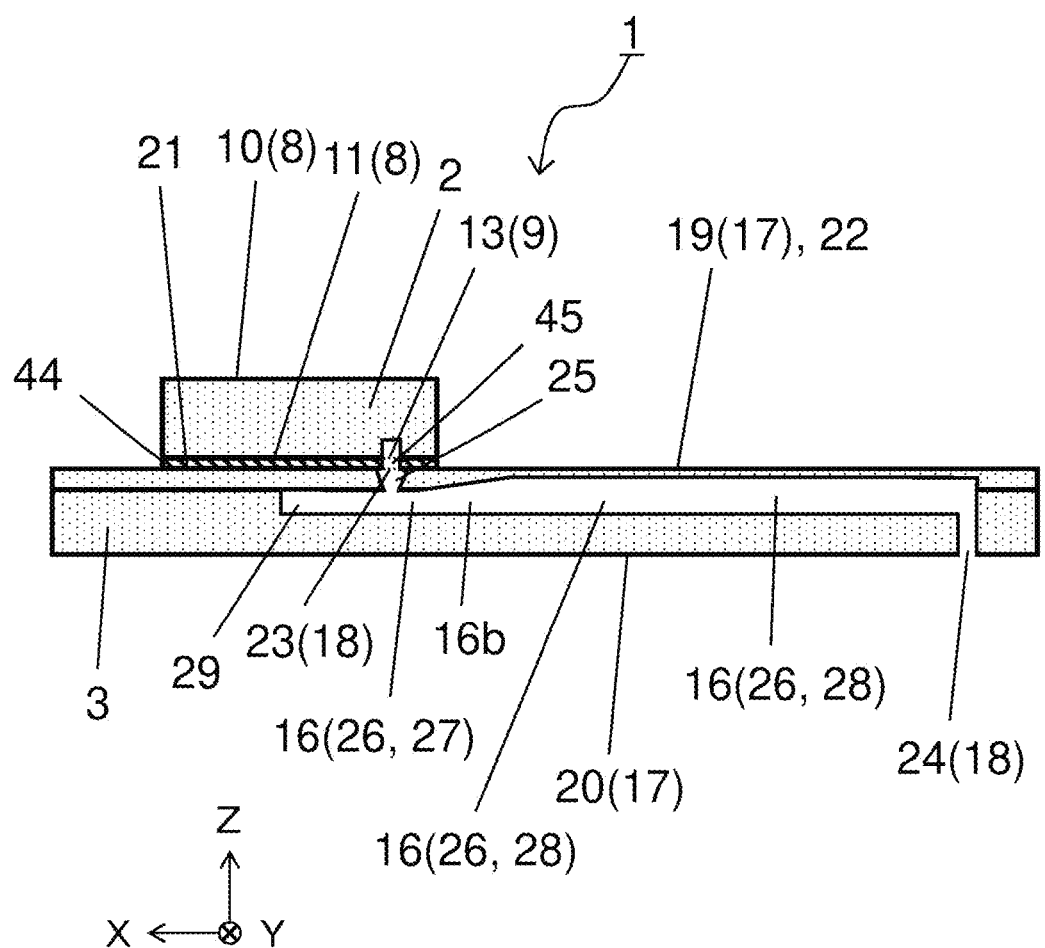
FIG. 10 illustrates a cross-sectional view of the example particle separating and measuring device according to the one embodiment of the present disclosure.

The second planar portion 28 may have a greater height (higher) than the first planar portion 27. As in a cross-sectional view of FIG. 10 similar to FIG. 2, the second flow path device 3 may include a height-increasing portion 16b between the first flow inlet 23 and the second planar portion 28 located in the second region 22 and used as the measurement portion in the first flow path 16. The height-increasing portion 16b has a flow path height increasing downstream along the flow of the first fluid. The height-increasing portion 16b causes a flow of the first fluid to spread in the height direction to disperse the target particles contained in the first fluid, thus reducing unevenness of the target particles for measurement. The flow path has a height increasing over a relatively short distance and thus allows a vortex to occur in the flow of fluid, facilitating agitation of the target particles. This facilitates the diffusion of the separated target particles (e.g., the first particles P1).

The first planar portion 27 may have a height of, for example, 0.2 to 1 mm. The second planar portion 28 may have a height of, for example, 1 to 5 mm. In the one embodiment of the present disclosure, the height-increasing portion 16b has a height gradually increasing at the joint between the first planar portion 27 and the second planar portion 28. In other words, the height-increasing portion 16b is flared in the height direction. For example, the first planar portion 27 may have a height of 0.5 mm, and the second planar portion 28 may have a height of 1 mm, with the flared portion being flared at about 45°.

For the structure including both the width-increasing portion 16a and the height-increasing portion 16b, the height-increasing portion 16b may be immediately upstream from the width-increasing portion 16a. The width-increasing portion 16a and height-increasing portion 16b may be closest possible to each other. In the flow path having the width greater than the height, the height-increasing portion may be upstream from the width-increasing portion. This structure allows the fluid to be vertically agitated in the height-increasing portion with a narrow width and then laterally agitated with the increasing width. This allows more uniform agitation. A width-increasing portion located upstream can reduce the effects of agitation in the height direction.

The second flow path device 3 may further include, in addition to the first flow path 16, a third flow path 29 connected to the first flow path 16. The third flow path 29 may be connected to the planar portion 26 in the first flow path 16. The third flow path 29 receives, for example, a gas for forcing out the fluid accumulating in the planar portion 26. This reduces fluid accumulation in the first flow path 16.

As shown in FIGS. 8 and 9, the third flow path 29 is connected to the joint between the connection flow path 25 and the planar portion 26 in the first flow path 16 in the second flow path device 3 according to the one embodiment of the present disclosure.

The third flow path 29 has one end connected to the first flow path 16. The third flow path 29 has the other end being a third opening 30 located in the pair of second upper and lower surfaces 17. More specifically, the third flow path 29 has the third opening 30 located in one of the pair of second upper and lower surfaces 17 (the second upper surface 19 in the one embodiment of the present disclosure). The third opening 30 receives a displacement fluid (e.g., gas) for forcing another fluid out of the second planar portion 28 in the first flow path 16.

As shown in FIG. 8, the third flow path 29 may have a portion connected to the first flow path 16 and at least partially extending along the extension of the planar portion 26 (the second planar portion 28) in the first flow path 16.

The third flow path 29 may have a portion connected to the first flow path 16 and at least partially having the same shape as a portion of the first flow path 16 connected to the third flow path 29. This eliminates a step at a joint between the first flow path 16 and the third flow path 29, reducing accumulation of the fluid at the joint.

As shown in FIG. 8, the third flow path 29 may include multiple straight portions 31 extending in a predetermined direction and arranged in a direction intersecting the direction. The third flow path 29 including the multiple straight portions 31 reduces the fluid flowing back from the first flow path 16 and leaking from the third opening 30.

The first openings 9 as the pre-separation flow inlet 12 and the post-separation flow outlet 13 may be in the same surface (the first lower surface 11 in the one embodiment of the present disclosure). In this case, a specimen flows into the first flow path device 2 from below (in the negative Z-direction). In this structure, the second particles P2 having a greater specific gravity than the first particles P1 sink and are thus easily separated.

As shown FIG. 8, the second flow path device 3 may further include a fourth flow path 32 different from the first flow path 16 and the third flow path 29. The fourth flow path 32 may have multiple fourth openings 33 located in one or both of the pair of second upper and lower surfaces 17. The fourth flow path 32 allows a specimen to flow before target particles are separated in the specimen. The fourth flow path 32 in the second flow path device 3 allows the specimen to flow to reduce foreign matter before entering the first flow path device 2.

The multiple fourth openings 33 include a fourth flow inlet 34 and a fourth flow outlet 35. The fourth flow inlet 34 is an opening for receiving the specimen to flow into the fourth flow path 32. The fourth flow outlet 35 is an opening for discharging the specimen from the fourth flow path 32. The fourth flow inlet 34 is open to receive the specimen from outside. The fourth flow outlet 35 is connected to the pre-separation flow inlet 12 in the first flow path device 2.

The fourth flow inlet 34 and the fourth flow outlet 35 may be in the second upper surface 19. In this case, an operator can handle the device from above for, for example, connecting the device with an external component to supply a specimen. In the one embodiment of the present disclosure, the fourth flow inlet 34 is in the same surface as the first flow outlet 24. In the one embodiment of the present disclosure, the fourth flow outlet 35 is also in the same surface as the first flow outlet 24. The fourth flow inlet 34 is in the same surface as the third opening 30.

As shown in FIG. 8, the second flow path device 3 may further include a second flow path 36 different from the first flow path 16, the third flow path 29, and the fourth flow path 32. The first flow path 16 is used for the first fluid containing the target particles separated and collected by the first flow path device 2, whereas the second flow path 36 is used for the second fluid free from the target particles. For example, the second flow path 36 is used for the second fluid for comparison or calibration for measuring the first fluid. The second fluid may be the same fluid as the first fluid but excluding the target particles, or may be a different fluid. For every measurement of the target particles, the first flow path 16 and the second flow path 36 may sequentially undergo measurement to determine the difference in light intensity between them. The difference can be used to estimate the number of target particles. The results are less susceptible to deterioration of the optical sensor.

The second flow path 36 has multiple fifth openings 37 located in the pair of second upper and lower surfaces 17. The fifth openings 37 include a second flow inlet 38 and a second flow outlet 39. The second flow inlet 38 is an opening for receiving the second fluid to flow into the second flow path 36. The second flow outlet 39 is an opening for discharging the second fluid from the second flow path 36. The second flow path 36 includes a measurement portion similarly shaped to the second planar portion 28 in the first flow path 16.

The second flow inlet 38 as one of the multiple fifth openings 37 is in the same surface as the third opening 30. In this case, an operator can handle the device on the same surface from above for, for example, supplying and discharging the second fluid. The second flow outlet 39 may be in the second lower surface 20.

The second flow path device 3 may further include a sixth flow path 40 different from the first flow path 16, the third flow path 29, the fourth flow path 32, and the second flow path 36. The sixth flow path 40 has multiple sixth openings 41 in one or both of the pair of second upper and lower surfaces 17. The multiple sixth openings 41 include a sixth flow inlet 42 and a sixth flow outlet 43. The sixth flow inlet 42 is an opening for receiving a fluid for generating a pressing flow to flow into the sixth flow path 40. The sixth flow outlet 43 is an opening for discharging the fluid for generating a pressing flow from the sixth flow path 40. The sixth flow inlet 42 is located to receive the fluid. The sixth flow outlet 43 is connected to the pressing-flow inlet 15 in the first flow path device 2.

The third flow path 29, the fourth flow path 32, the second flow path 36, and the sixth flow path 40 may be formed in the same manner as the first flow path 16.

Particle Separating Apparatus

A particle separating apparatus in the particle separating and measuring apparatus according to the one embodiment of the present disclosure will now be described. The particle separating apparatus according to the one embodiment of the present disclosure includes the first flow path device 2 as a particle separating device, a first pump for pumping a specimen into the pre-separation flow inlet 12, and a second pump for pumping a fluid into the pressing-flow inlet 15. The particle separating device is the first flow path device 2 described above. The first flow path device 2 has the pre-separation flow inlet 12 connected to the first pump with, for example, a first tube. The first pump delivers a specimen, which then flows through the first tube into the pre-separation flow inlet 12 in the first flow path device 2. The first flow path device 2 has the pressing-flow inlet 15 connected to the second pump with, for example, a second tube. The second pump delivers a fluid, which flows through the second tube into the pressing-flow inlet 15 in the first flow path device 2.

This structure allows target particles (e.g., the first particles P1) to be separated and collected from the specimen through the main flow path 5 and the multiple branch flow paths 6, as described above.

The first and second pumps may be any of a variety of known pumps that can pump a fluid. The first pump may be capable of pumping a small amount of fluid (e.g., blood) containing particles into the pre-separation flow inlet 12 in the first flow path device 2 at a constant flow velocity. The second pump may be capable of pumping a fluid for generating a pressing flow (e.g., phosphate buffered saline, or PBS) into the pressing-flow inlet 15 in the first flow path device 2 at an appropriate flow rate, flow velocity, and pressure. The first and second pumps may be, for example, syringe pumps. Other pumps such as electroosmotic pumps, peristaltic pumps, and gas pumps may also be used.

The first and second tubes may be formed from any of a variety of known materials in accordance with the fluid to be used. For example, silicone tubes may be used for blood as the specimen and PBS as the fluid. These tubes are optional and may be eliminated when, for example, the first flow path device 2 is connected to the first and second pumps directly or with adapters.

Particle Separating and Measuring Apparatus

A particle separating and measuring apparatus according to the one embodiment of the present disclosure will now be described. The apparatus includes the particle separating and measuring device according to the one embodiment of the present disclosure.

Figure 11:
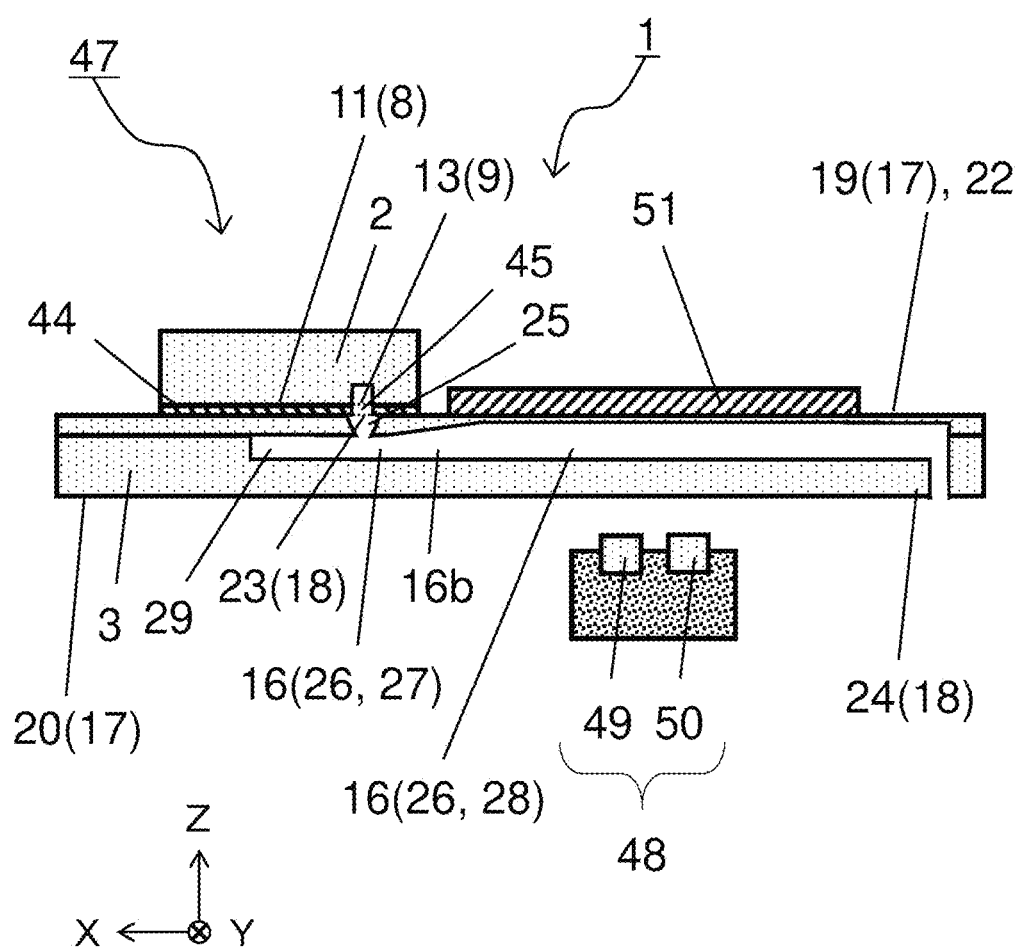
FIG. 11 illustrates a cross-sectional view of an example particle separating and measuring apparatus including the particle separating and measuring device according to the one embodiment of the present disclosure.
Figure 12:
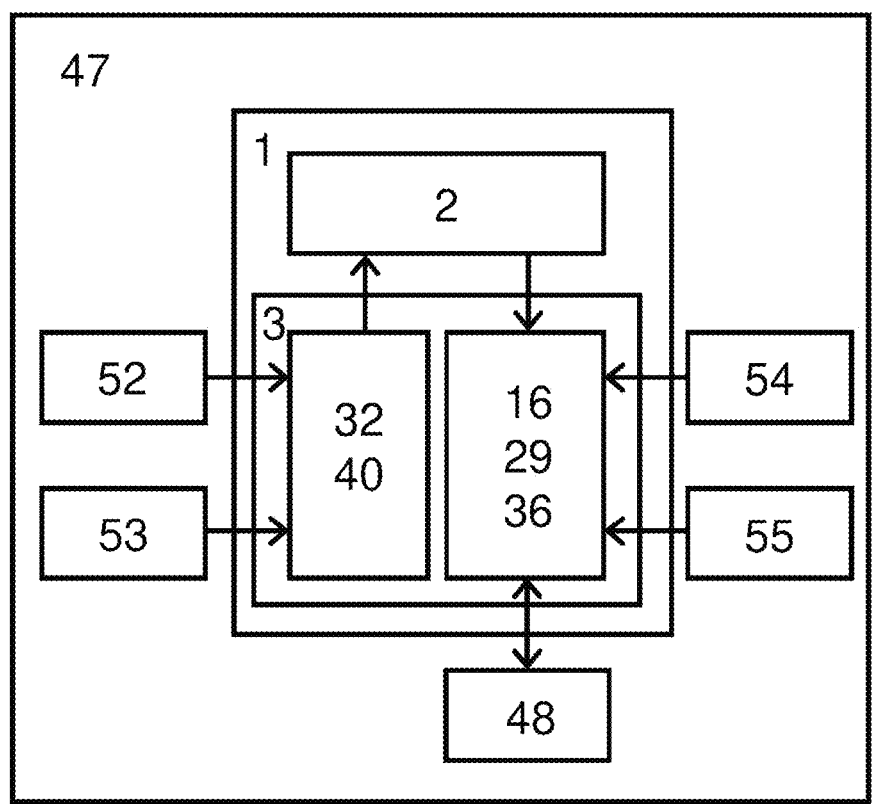
FIG. 12 illustrates a block diagram of the particle separating and measuring apparatus according to the one embodiment of the present disclosure, showing its example overall structure.

FIGS. 11 and 12 schematically show a particle separating and measuring apparatus 47. FIG. 11 is a cross-sectional view of the particle separating and measuring apparatus 47 as viewed from the same viewpoint as FIGS. 2 and 10. Some reference numerals are the same as those in FIGS. 2 and 10 and thus are not described. FIG. 12 is a block diagram of the particle separating and measuring apparatus 47, showing its example overall structure.

The particle separating and measuring apparatus 47 includes the particle separating and measuring device 1 and an optical sensor 48. The optical sensor 48 includes a light-emitting element 49 and a light receiving element 50. The first flow path device 2 in the particle separating and measuring device 1 separates intended target particles (e.g., the first particles P1) in the specimen. The target particles then flow into the first flow path 16 (the second planar portion 28) in the second flow path device 3 in the particle separating and measuring device 1. The optical sensor 48 emits light with the light-emitting element 49 toward the target particles, and receives, with the light receiving element 50, light passing through the first flow path 16 (the second planar portion 28) for measurement of the particles. More specifically, the light passing through the first flow path 16 is scattered, reflected, or absorbed by the particles (the first particles P1) in the first fluid and is thus attenuated in intensity. A calibration curve is predefined to show the relationship between the specimen having a known number of particles and the corresponding attenuation of light. The particles in the specimen can be measured by comparing the attenuation of received light measured by the particle separating and measuring apparatus 47 with the calibration curve.

The particle separating and measuring apparatus 47 according to the one embodiment of the present disclosure includes the particle separating and measuring device 1 according to the one embodiment of the present disclosure described above, the optical sensor 48, and a controller. The optical sensor 48 emits light toward the measurement portions in the first flow path 16 and the second flow path 36 in the particle separating and measuring device 1, and receives light passing through the measurement portions in the first flow path 16 and the second flow path 36. The controller measures target particles by comparing the intensity of the light passing through the measurement portion in the first flow path 16 and received by the optical sensor 48 with the intensity of the light passing through the measurement portion in the second flow path 36 and received by the optical sensor 48.

The light-emitting element 49 may be, for example, a light-emitting diode (LED). The light receiving element 50 may be, for example, a photodiode (PD). For example, the light receiving element 50 is a PD formed on the upper surface of a semiconductor substrate and having regions of one conductivity type and another conductivity type. The light-emitting element 49 is an LED including multiple semiconductor layers stacked on the semiconductor substrate.

The particle separating and measuring device 1 in the particle separating and measuring apparatus 47 according to the one embodiment of the present disclosure includes a mirror 51 located in the second region 22 in the second upper surface 19 of the second flow path device 3. The optical sensor 48 has the light-emitting element 49 and the light receiving element 50 located adjacent to the second lower surface 20 of the second flow path device 3. Thus, light emitted from the light-emitting element 49 in the optical sensor 48 passes through the first flow path 16 (the second planar portion 28), is reflected by the mirror 51, and is then received by the light receiving element 50 in the optical sensor 48. The mirror 51 may be formed from, for example, aluminum or gold. The mirror 51 may be formed by, for example, depositing a metal foil with vapor deposition or sputtering.

The particle separating and measuring apparatus 47 further includes a first supply unit 52 for supplying a specimen, a second supply unit 53 for supplying a fluid for generating a pressing flow, a third supply unit 54 for supplying a displacement fluid, and a fourth supply unit 55 for supplying the second fluid as a calibration fluid. The first to fourth supply units 52 to 55 are connected to the particle separating and measuring device 1. The first supply unit 52 is connected to the fourth flow inlet 34. The second supply unit 53 is connected to the sixth flow inlet 42. The third supply unit 54 is connected to the third opening 30. The fourth supply unit 55 is connected to the second flow inlet 38. The particle separating and measuring apparatus 47 includes a controller (not shown) for controlling the first supply unit 52, the second supply unit 53, the third supply unit 54, the fourth supply unit 55, and the optical sensor 48.

The particle separating and measuring apparatus 47 according to the one embodiment of the present disclosure includes the particle separating and measuring device 1 according to the one embodiment of the present disclosure. Thus, the particle separating and measuring apparatus 47 separates target particles in a specimen for accurate and reliable measurement.

The present disclosure is not limited to the above embodiments, but may be changed and modified variously without departing from the spirit and scope of the present disclosure.

Figure 13:
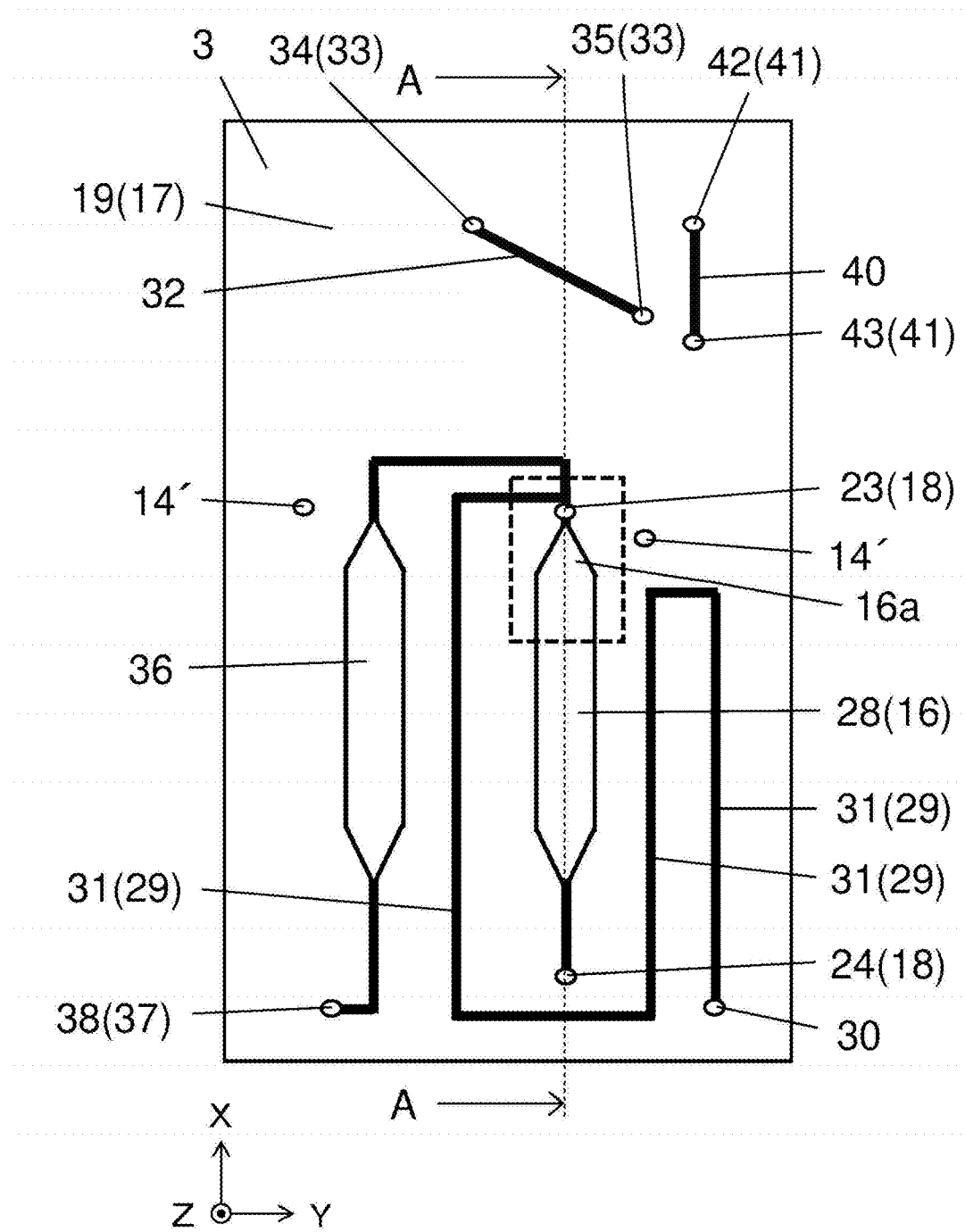
FIG. 13 illustrates a plan view of an example second flow path device in the particle separating and measuring device according to the one embodiment of the present disclosure.
Figure 14:
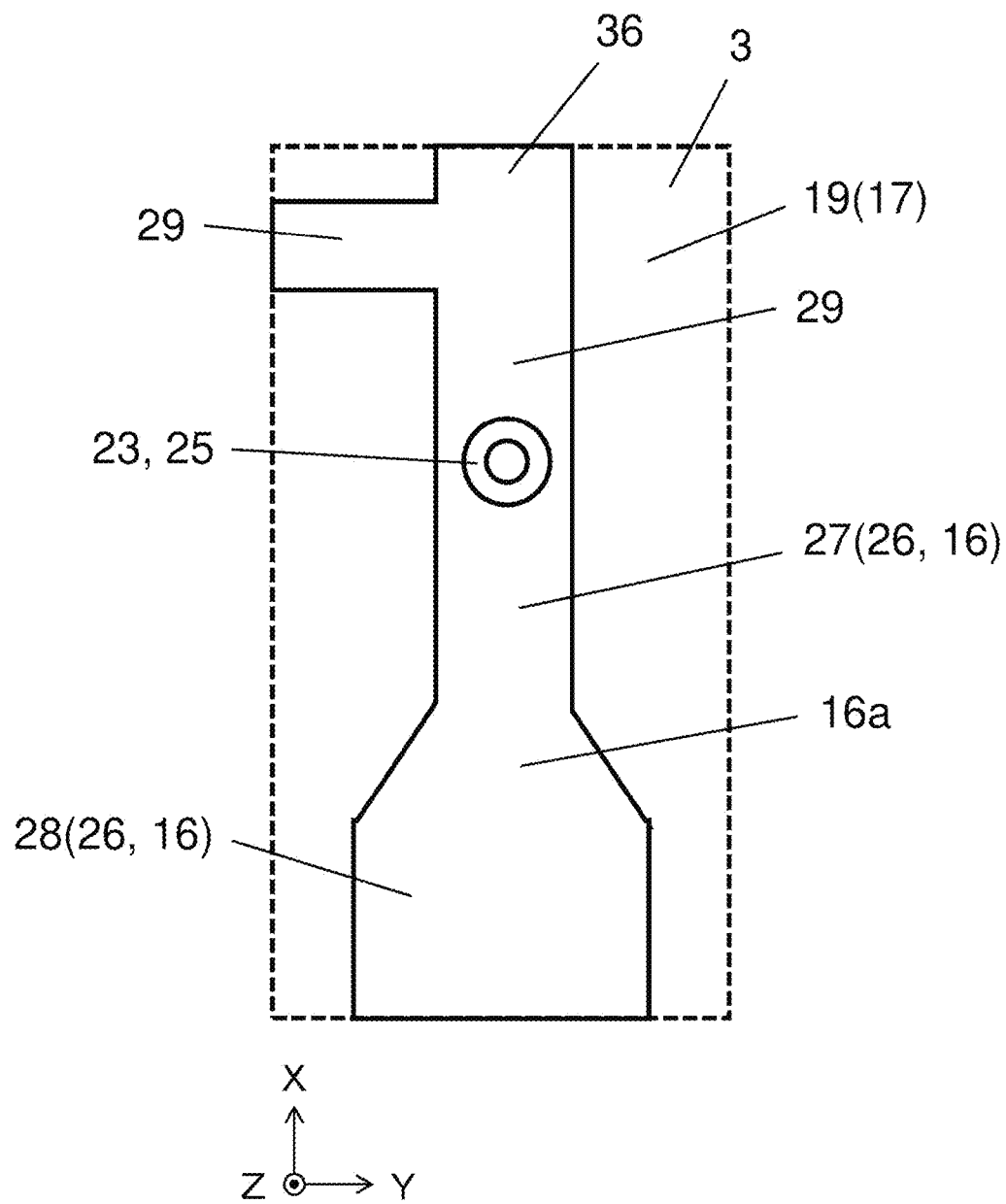
FIG. 14 illustrates a partial plan view of the example second flow path device in the particle separating and measuring device according to the one embodiment of the present disclosure.

In the above embodiments, the second flow path 36 has one end being the second flow outlet 39. In some embodiments, the second flow path 36 may have one end connected to the first flow path 16 as shown in FIGS. 13 and 14. This structure allows the second fluid in the second flow path 36 to be injected into the first flow path 16 to reduce the density of target particles (e.g., leukocytes) contained in the first fluid in the first flow path 16. FIGS. 13 and 14 are similar to FIGS. 8 and 9 as viewed from a similar viewpoint, and are not described in detail.

In the above embodiments, the second flow path device 3 includes the second flow path 36 and the sixth flow path 40. In some embodiments, the second flow path 36 may serve as the sixth flow path 40. More specifically, the second flow path 36 and the sixth flow path 40 may be formed as a single flow path and connected to the separating flow path 4 (the pressing-flow inlet 15).

The invention claimed is:

1. A particle separating and measuring device, comprising:
   a first flow path device that is plate-shaped, and including
      a pre-separation flow inlet configured to receive a fluid containing target particles to be separated,
      a main flow path connected to the pre-separation flow inlet,
      a plurality of branch flow paths connected to the main flow path, and
      a post-separation flow outlet configured to discharge a first fluid containing the target particles after being separated; and
   a second flow path device that is plate-shaped, and including
      a first region configured to receive the first flow path device,
      a second region configured to measure the target particles,
      a first flow inlet configured to receive the first fluid,
      a second flow inlet configured to receive a second fluid free from the target particles,
      a first flow path located in the second region and connected to the first flow inlet to allow a flow of the first fluid, and
      a second flow path located in the second region and connected to the second flow inlet to allow a flow of the second fluid;
   wherein a lower surface of the first flow path device includes the post-separation flow outlet, and an upper surface of the second flow path device includes the first flow inlet in the first region, and the post-separation flow outlet faces and connects to the first flow inlet, and
   wherein the second flow path device has a connection flow path vertically extending from an opening of the first flow inlet to the first flow path, and the connection flow path having an inclined inner wall narrows from the opening of the first flow inlet toward the first flow path.

2. The particle separating and measuring device according to claim 1, wherein the opening of the first flow inlet is larger than an opening of the post-separation flow outlet.

3. The particle separating and measuring device according to claim 1, wherein the opening of the first flow inlet is circular, and the connection flow path has a circular cross section.

4. The particle separating and measuring device according to claim 1, wherein
   the first flow path device is on the second flow path device with a sheet member therebetween, and
   a through-hole in the sheet member connects the post-separation flow outlet and the first flow inlet.

5. The particle separating and measuring device according to claim 4, wherein
   the through-hole narrows from the post-separation flow outlet toward the first flow inlet.

6. The particle separating and measuring device according to claim 1, wherein the second flow path device includes a width-increasing portion having a flow path width increasing downstream along the flow of the first fluid from a joint between the connection flow path and the first flow path.

7. The particle separating and measuring device according to claim 1, wherein
   the opening of the first flow inlet connects to an opening of the post-separation flow outlet at the upper surface of the second flow path device, and
   a diameter of the opening of the first flow inlet is larger than a diameter of the opening of the post-separation flow outlet.

8. A particle separating and measuring apparatus, comprising:
   a particle separating and measuring device including:
      a first flow path device that is plate-shaped, and including
         a pre-separation flow inlet configured to receive a fluid containing target particles to be separated,
         a main flow path connected to the pre-separation flow inlet,
         a plurality of branch flow paths connected to the main flow path, and
         a post-separation flow outlet configured to discharge a first fluid containing the target particles after being separated; and
      a second flow path device that is plate-shaped, and including
         a first region configured to receive the first flow path device,
         a second region configured to measure the target particles,
         a first flow inlet configured to receive the first fluid,
         a second flow inlet configured to receive a second fluid free from the target particles,
         a first flow path located in the second region and connected to the first flow inlet to allow a flow of the first fluid, and
         a second flow path located in the second region and connected to the second flow inlet to allow a flow of the second fluid;
      wherein a lower surface of the first flow path device includes the post-separation flow outlet, and an upper surface of the second flow path device includes the first flow inlet in the first region, and the post-separation flow outlet faces and connects to the first flow inlet, and
      wherein the second flow path device has a connection flow path vertically extending from an opening of the first flow inlet to the first flow path, and the connection flow path having an inclined inner wall narrows from the opening of the first flow inlet toward the first flow path;
   an optical sensor configured to emit light toward the first flow path and the second flow path in the particle separating and measuring device, and receive light passing through the first flow path and the second flow path; and
   a controller configured to measure the target particles by comparing an intensity of the light passing through the first flow path and received by the optical sensor with an intensity of the light passing through the second flow path and received by the optical sensor.

* * * * *